United States Patent [19]
Olney et al.

[11] Patent Number: 5,902,815
[45] Date of Patent: May 11, 1999

[54] USE OF 5HT-2A SEROTONIN AGONISTS TO PREVENT ADVERSE EFFECTS OF NMDA RECEPTOR HYPOFUNCTION

[75] Inventors: John W. Olney, Ladue; Nuri B. Farber, University City, both of Mo.

[73] Assignee: Washington University, St. Louis, Mo.

[21] Appl. No.: 08/709,222

[22] Filed: Sep. 3, 1996

[51] Int. Cl.$^6$ ......................... A61K 31/445; A61K 31/54; A61K 31/135

[52] U.S. Cl. .......................... 514/285; 514/315; 514/318; 514/646

[58] Field of Search ............................ 514/285; 314/315, 314/318, 646

[56] References Cited

U.S. PATENT DOCUMENTS

| | | | |
|---|---|---|---|
| 5,034,400 | 7/1991 | Olney | 514/315 |
| 5,474,990 | 12/1995 | Olney et al. | 514/226 |
| 5,605,911 | 2/1997 | Olney et al. | 514/315 |
| 5,629,307 | 5/1997 | Olney et al. | 514/226 |

OTHER PUBLICATIONS

Caldwell, M.A. et al, "The dopamine agonists lisuride and piribedil protect against behavioural and histological changes following 4–vessel occlusion in the rat," *Neuropsychobiology* 34: 117–24 (1996).

Calne, D.B. "Initiating treatment for idiopathic parkinsonism" *Neurology* 44: S19–S22 (1994).

Carlsson, M.L. "The selective 5–HT2A receptor antagonist MDL 100,907 counteracts the psychomotor stimulation ensuing manipulations with manoaminergic glutamatergic or muscarinic neurotransmission in the mouse—implications for psychosis" *Journal of Neural Transmission 100*: 225–237 (1995).

Eblen, F. et al, "Effects of 7–nitroindazole, NG–nitro–L–arginine, and D–CPPene on harmaline–induced postural tremor, N–methyl–D–aspartate–induced seizures, and lisuride–induced rotations in rats with nigral 6–hydroxydopamine lesions," *Eur J Pharmacol* 299 : 1–3 (1996).

Fink, H. et al "Locomotor effects of lisuride: A consequence of dopaminergic and serotonergic actions" *Psychopharmacology* 85: 464–468 (1985).

Fiorella, D. et al, Role of 5–HT2A and 5–HT2C receptors in the stimulus effects of hallucinogenic drugs. II: Reassessment of LSD false positives. *Psychopharmacology* 121: 357–63 (1995) (abstract).

Glennon, R.A. "Do Classical Hallucinogens Act As 5–HT2 Agonists of Antagonists?" *Neuropsychopharmacology 3*: 509–517 (1990).

Heinz, A. et al, "Clinical aspects and follow–up of dopamine–induced psychoses in continuous dopaminergic therapy and their implications for the dopamine hypothesis of schizophrenic symptoms" *Nervenarzt* 66: 662–9 (1995) (abstract).

Heinz, A. et al, "Continuous subcutaneous lisuride infusion in OPCA" *Journal of Neural Transmission 90*: 145–150 (1992).

Hougaku, H. et al, "Therapeutic effect of lisuride maleate on post–stroke depression" *Nippon Ronen Igakkai Zasshi 31*: 52–9 (1994) (abstract).

Kehne, J.H. et al, "Preclinical Characterization of the Potential of the Putative Atypical Antipsychotic MDL 100,907 as a Potent 5–HT2A Antagonist with a Favorable CNS Saftey Profile" *The Journal of Pharmacology and Experimental Therapuetics 277*: 968–981 (1996).

Maurel–Remy, S. et al, "Blockade of phencyclidine–induced hyperlocomotion by clozapine and MDL 100,907 in rats reflects antagonism of 5–HT2A receptors" *European Journal of Pharmacology 280*: R9–R11 (1995).

Olney, J.W., et al, "NMDA antagonist neurotoxicity: Mechanism and prevention," *Science* 254: 1515–1518 (1991).

Olney, J.W., et al, "Glutamate receptor dysfunction and schizophrenia," *Arch. Gen. Psychiatry* 52: 998–1007 (1995).

Pulvirenti, L. et al, "Dopamine receptor agonists, partial agonists and psychostimulant addiction" *Trends Pharmacol Sci 15*: 374–9 (1994).

Robles, R.G. et al, "Natriuretic Effects of Dopamine Agonist Drugs in Models of Reduced Renal Mass" *Journal of Cardiovascular Pharmacology 22* (*Suppl.* 2): S88–S92 (1993).

(List continued on next page.)

Primary Examiner—Keith D. MacMillan
Attorney, Agent, or Firm—Patrick D. Kelly

[57] ABSTRACT

This invention relates to a new method for treating or preventing brain damage caused by NMDA receptor hypofunction (NR/hypo), using drugs such as lisuride which stimulate (agonize) activity at the 5HT-2A class of serotonin receptors, but which do not cause hallucinations. Data disclosed herein indicate that stimulation of both 5HT-2A and 5HT-2C receptors causes hallucinations, while stimulation of 5HT-2A receptors but not 5HT-2C receptors does not. Accordingly, to be useful herein, non-hallucinatory 5HT-2A agonists should either (1) antagonize (suppress) activity at 5HT-2C receptors, or (2) have no significant effect on activity at 5HT-2C receptors. Selective non-hallucinatory 5HT-2A agonists can be used in either of two treatment methods disclosed herein.

One such treatment comprises administering a 5HT-2A receptor agonist as a "safener drug" which accompanies an NMDA antagonist drug that is being used for a therapeutic purpose.

Another method disclosed herein involves the use of a 5HT-2A agonist drug, by itself, to combat a naturally-occurring form of NMDA receptor hypofunction which occurs in people suffering from schizophrenia. Although 5HT-2A agonists would not be optimally effective in treating long-standing cases of chronic schizophrenia, where pathological changes in the brain have already reached maximal or severe levels, 5HT-2A agonists can be administered early in the illness, such as at the first signs of schizophrenic illness, and continuously thereafter to prevent the development or worsening of pathological brain dysfunction and the resulting psychosis.

14 Claims, 3 Drawing Sheets

OTHER PUBLICATIONS

Rosenfeld, M.R. et al, "The Interaction of Lisuride, and Ergot derivative with Serotonergic and Dopaminergic Receptors in Rabbit Brain" *The Journal of Pharmacology and Experimental Therapeutics 216*: 526–531 (1980).

Schmidt, C.J. et al, "The role of 5–HT2A receptors in antipsychotic activity" *Life Sciences 56*: 2209–2222 (1995).

Stocchi, F. et al, "Apomorphine and Lisuride Infusion" *Advances in Neurology 60*: 653–655 (1993).

Varty, G.B. et al, "Reversal of a dizocilpine–induced disruption of prepulse inhibition of an acoustic startle response by the 5–HT2 receptor antagonist ketanser" *European Journal of Pharmacology 287*: 201–205 (1995).

Chemical Abstracts AN 1992:563764, Wachtel et al, 1992.

□ MK-801 plus DOI

△ MK-801 plus DOI plus ritanserin

USE OF 5HT-2A SEROTONIN AGONISTS TO PREVENT ADVERSE EFFECTS OF NMDA RECEPTOR HYPOFUNCTION

GOVERNMENT SUPPORT

The research which led to this invention was supported in part by grants from the National Institutes of Health, including grants AG 11355, DA 05072, DA 00290, and MH 38894. Accordingly, the federal government has certain rights in this invention.

BACKGROUND OF THE INVENTION

The present invention relates to neurology and pharmacology, and to drugs for treating or preventing problems in the central nervous system (CNS). More specifically, this invention involves drugs that activate a certain type of receptor in the brain which is normally activated by serotonin. This receptor is called the 5HT-2A receptor.

The following Background sections provide introductory information on several types of receptors on the surfaces of neurons inside the brain, and on various neurotransmitters and drugs that stimulate or suppress activity at these receptors. Although the drugs that are the subject of this invention stimulate certain serotonin receptors, these drugs are intended to solve problems involving an entirely different class of receptors, triggered by glutamate. Therefore, glutamate receptors are described first, followed by serotonin receptors.

Glutamate (GLU) and Its Receptors; Agonists and Antagonists

Glutamate (sometimes abbreviated as GLU) is one of the 20 common amino acids used by all living cells to make protein. Glutamate is the ionized form of glutamic acid, and is the predominant form in neutral solutions, at pH 7.

In addition to its role as a building block in proteins, glutamate also plays an entirely distinct and crucial role in the central nervous system (CNS) of higher animals, including mammals and birds. Within the CNS, glutamate serves as the predominant excitatory neurotransmitter (e.g., Olney 1987; full citations to books and articles are provided below).

In a brief overview, this process can be summarized as follows. At a neuronal synapse (i.e., a signal-transmitting junction between two nerve cells), a molecule of glutamate is released by the signal-transmitting neuron. The glutamate molecule enters the fluid in the gap between the two neurons, and it quickly contacts the exposed portion of a glutamate receptor on the surface of the signal-receiving neuron. This receptor is a protein molecule that straddles the cellular membrane of the signal-receiving neuron.

A "receptor" as used herein refers to a macromolecular binding site which is at least partially exposed on the surface of a cell, and which has specific and limited affinity for one or more fluid-borne molecules called "ligands" (these usually are neurotransmitters or hormones). When a ligand contacts an appropriate receptor, a brief binding reaction occurs which triggers or otherwise evokes a cellular response, such as activation and depolarization of a neuron. Most receptor molecules are proteins which straddle the membrane of a cell, with an external portion for binding reactions and an internal portion which helps carry out the cellular response that occurs when the receptor is activated by a ligand.

This is not a rigid definition, and different scientists sometimes use the term "receptor" inconsistently; for example, they may either include or exclude various additional components, such as an ion channel which is opened or closed by a receptor.

Upon being activated (excited) by the glutamate molecule, the glutamate receptor changes its conformation, in a manner which briefly opens an ion channel that serves as a conduit through the cell membrane. Calcium ($Ca^{++}$), sodium ($Na^+$), and certain other types of ions immediately flow through the ion channel, thereby altering a chemical ionic gradient that normally exists across the membrane of the neuron. This activates the neuron, causing it to release its own neurotransmitters at other ("downstream") synapses, thereby transmitting nerve signals to still other neurons.

To reset the mechanism and get both the transmitting neuron and the receiving neuron back to a resting/ready condition, where both are ready to handle another nerve signal, the ion channel quickly closes, and the glutamate receptor protein on the signal-receiving neuron releases the glutamate molecule. The glutamate molecule floats back into the synaptic fluid between the neurons, and a molecular transport system quickly intercepts it and transports it back inside the transmitting neuron. The signal-receiving neuron activates a set of molecular pumps, which rapidly transport calcium and sodium ions (which had entered the cell though the glutamate-controlled ion channel) back out of the neuron to regain a "polarized" condition, so that it will be ready to receive another nerve signal.

This entire set of chemical actions—release of glutamate by a transmitting neuron, activation and depolarization of a signal-receiving neuron, release of the glutamate transmitter molecule by the receptor protein, clearance of the free glutamate from the synaptic fluid, and restoration of the polarized/ready state in the signal-receiving neuron—is extraordinarily rapid. All of these steps, together, occur within a few milliseconds.

Since glutamate is an amino acid that can function as an excitatory neurotransmitter inside the brain, it is often called an "excitatory amino acid" (EAA). Another type of amino acid, aspartate (the ionized form of aspartic acid), can also function as an excitatory amino acid in the brain; therefore, glutamate receptors are sometimes referred to as "EAA" receptors, since they can be triggered by either of two amino acids (glutamate or aspartate). However, glutamate is used much more widely than aspartate as a neurotransmitter, and EAA receptors (including both NMDA and non-NMDA receptors, discussed below) are referred to herein (and by most scientists) as glutamate or GLU receptors.

In pharmacological terminology, an "agonist" is a molecule which activates a certain type of receptor. For example, glutamate molecules act as agonists when they excite EAA receptors. By contrast, an "antagonist" is a molecule which prevents or reduces the effects exerted by an agonist at a receptor. In general, most naturally occurring neurotransmitters are agonists, since they activate the receptors they interact with. By contrast, artificial/exogenous drugs might be either agonists, or antagonists.

Types of GLU Receptors: NMDA and non-NMDA Receptors

There are three distinct types of glutamate receptors on the surfaces of mammalian neurons. Although all three receptor types are normally triggered by exactly the same EAA neurotransmitters in the brain (i.e., glutamate or aspartate), these three different subtypes of glutamate receptors have different patterns of distribution in the brain, and different binding properties when certain types of artificial drugs are used as probes to study neuronal activity.

One major class of GLU receptors is referred to as NMDA receptors, since they bind preferentially to NMDA, the acronym for n-methyl-D-aspartate. NMDA is a chemical analog of aspartic acid; it normally does not occur in nature, and NMDA is not present in the brain. It also is not a useful therapeutic drug; it would cause convulsions if administered to a human or lab animal. When molecules of NMDA contact neurons having NMDA receptors, they strongly activate the NMDA receptors and act as a powerful glutamate agonist, causing the same type of neuronal excitation that glutamate causes. Nevertheless, NMDA is a useful probe drug, which is widely used by neurologists to evaluate various types of neuronal excitation, and to test drugs which might be able to prevent or reduce certain types of damage to the brain or other portions of the CNS.

The second class of glutamate receptors is called kainic acid receptors, since they are activated by kainic acid (or by its ionized form, kainate). As with NMDA, the compound kainic acid does not occur in the brain, and it is not a useful therapeutic drug, since it too would cause convulsions if administered to a human or lab animal. However, kainic acid is useful as a probe drug, because it selectively binds to and activates a certain subclass of glutamate receptors, which accordingly are called kainic acid (KA) receptors.

The third subclass of GLU receptors is referred to herein as AMPA receptors; they are activated by both quisqualic acid (and its ionized form, quisqualate) and by alpha-amino-3-hydroxy-5-methyl-4-isoxazole (abbreviated as AMPA). Until the mid-to-late 1980's, AMPA receptors were usually called quisqualate (QUIS) receptors. However, quisqualate also activates a different type of receptor, called a metabotropic receptor, so the recent trend is to call QUIS-type EAA receptors by the name "AMPA receptors".

KA receptors and AMPA receptors are more closely related to each other (both structurally, and by higher levels of shared affinity to certain drugs) than to NMDA receptors. Accordingly, KA receptors and AMPA receptors are often referred to collectively as "non-NMDA receptors".

All three types of glutamate receptors (NMDA, KA, and AMPA) are "ionotropic" receptors, since they all control ion channels. These ion channels allow ions to flow into a neuron, thereby activating (depolarizing) the neuron, when the receptor is activated by glutamate, aspartate, or an agonist drug.

The NMDA receptor complex (which includes its ion channel) has a number of distinct binding sites (also called recognition sites), where several different substances can bind and thereby modify the action of glutamate. Thus, there are several different types of NMDA antagonists, each type being defined in terms of the binding site with which it interacts.

Competitive NMDA antagonists compete with glutamate at the glutamate binding site (which is also the NMDA binding site). The action of glutamate at this site promotes opening of the ion channel to allow $Na^+$ and $Ca^{++}$ ions to flow into the cell. Competitive antagonists block the action of glutamate at this site, and prevent opening of the ion channel; thus, they are often referred to as "closed channel blockers." Competitive NMDA antagonists being developed by drug companies are usually given acronyms or code numbers, and they include, but are not limited to, compounds such as CPP (Boast 1988), D-CPP-ene (Herrling 1994), CGP 40116 and CGP 37849 (Fagg et al 1990), CGS 19755 (Boast 1988 and Grotta 1995), NPC 12626 (Ferkany et al 1989), and NPC 17742 (Ferkany et al 1993). Other competitive NMDA antagonists include D-AP5 (D-2-amino-5-phosphonopentanoic acid), D-AP7, CGP 39551 (D,L(E)-2-amino-4-methyl-5-phosphono-3-pentenoic acid carboxyethyl ester), CGP-43487, MDL-100,452, LY-274614, LY-233536, LY-233053. Regrettably, even though these drugs held early promise for possibly reducing brain damage caused by stroke, cardiac arrest, etc., most of these drugs have been shown to cause pathomorphological changes in certain regions of the mammalian brain, in lab animals (Olney et al 1991; Hargreaves et al 1993). All of these drugs that have been tested in adult humans have also been shown to cause psychotomimetic reactions, such as hallucinations; this suggests a connection between the psychotomimetic effects and the brain-damaging effects of these drugs, and that similar types of damage in certain vulnerable regions of the brain may also occur in humans when competitive NMDA antagonists are administered (Grotta 1995; Herrling 1994; Kristensen et al 1992).

There are also other sites in the NMDA receptor complex, located outside the ion channel, where glycine or certain types of polyamines can bind. Binding of glycine and polyamines to these sites exerts a cooperative action that assists glutamate in opening the ion channel. Accordingly, it is hoped and believed by some that drugs which block the glycine or polyamine sites may have neuroprotective actions which are comparable to, but somewhat milder than, competitive antagonists which act at the glutamate binding site. Glycine and polyamine site antagonists include but are not limited to kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715. For reviews and citations, see Carter et al 1988, Rogawski 1992, and Massieu et al 1993.

Within the NMDA receptor ion channel, there is a site where phencyclidine (PCP) and several other drugs (including dizocilpine, ketamine, tiletamine, and CNS 1102) bind selectively. When these agents bind to the PCP site in the ion channel, they block ion flow through the channel, even if the channel otherwise remains open: thus, drugs that block activity at NMDA receptors by binding to the PCP site are sometimes referred to as "open channel blockers".

Dizocilpine is the most selective and effective non-competitive NMDA antagonist ever discovered; it is powerful and highly selective at the PCP binding site. The full chemical name is (+)-5-methyl-10,11-dihydro-5H-di[a,d] cyclohepten-5,10-imine. The maleate salt of dizocilpine is commercially available to researchers under the name MK-801, and MK-801 has been investigated extensively for use as an antiepileptic and for preventing damage due to cerebral ischemia. However, it has been shown, even at relatively low doses, to produce pathomorphological changes in cerebrocortical neurons in adult rats (Olney et al 1989).

Phencyclidine is a dissociative anesthetic, formerly used in human and veterinary medicine, that is illicitly abused as a hallucinogenic drug under the street name "angel dust". This drug can induce a psychosis which is clinically indistinguishable from schizophrenia, and it has been shown at relatively low doses to produce pathomorphological changes in various corticolimbic regions of the adult rat brain (Olney et al 1989, Corso et al 1994).

Ketamine, a dissociative anesthetic, is the only NMDA antagonist that is currently approved for use on humans. It is no longer widely used, since anesthesiologists have become aware of the toxic side effects of NMDA antagonists; however, it has a very short duration of action (usually only about 15 minutes), so its anesthetic effects can be rapidly reversed by terminating intravenous administration. Therefore, it is still occasionally used. Despite its short duration of action, it sometimes produces an "emergence" reaction during recovery from anesthesia that is characterized by unpleasant dreams, confusion, agitation, hallucinations, and irrational behavior. Ketamine has recently been studied for its psychotomimetic effects and has been described as an agent that produces symptoms in normal humans that are indistinguishable from the symptoms of psychosis and thought disorder seen in schizophrenia (Krystal et al 1994). Ketamine also has been shown to cause pathomorphological changes in the cerebral cortex of adult rats (Olney et al 1989).

Tiletamine, also used in veterinary medicine as an anesthetic, is another non-competitive NMDA antagonist which acts at the PCP binding site. It has also been shown to cause pathomorphological changes in the cerebral cortex of adult rats (Olney et al 1989).

Toxic Effects of Excessive NMDA Receptor Activity; Utility of NMDA Antagonists

Excessive activation of NMDA receptors by endogenous glutamate is thought to play a major role in a number of important CNS disorders. In an acute crisis such as a stroke or CNS trauma, and in certain other events such as severe epileptic seizures, the cellular transport mechanism that removes glutamate almost immediately from the synaptic fluid, and pumps it back inside a neuron for subsequent re-use, can run out of energy to drive the glutamate clearance process. If this occurs, excessive glutamate begins to accumulate in the synaptic fluid between neurons. If glutamate molecules are not being removed from synapses at adequate rates, they begin to repeatedly and persistently excite glutamate receptors on signal-receiving neurons. This drives the receptor-bearing neurons into a state of hyper-excitation which can kill the neurons, through a process called "excitotoxicity" (e.g., Olney 1990a, Choi 1988, Choi 1992).

Excessive activity at NMDA receptors can also severely aggravate neuronal damage caused by trauma (mechanical injury) to the brain or spinal cord. Many trauma victims suffer from a dangerous and potentially lethal increase in intracranial pressure, which involves water flowing into neurons in an effort to sustain osmotic balance as charged ions flow into the neurons during neuronal excitation. Elevated intracranial pressure is a major cause of morbidity and mortality in CNS trauma victims, and NMDA antagonists are potentially useful in reducing intracranial pressure following such crises.

As used herein, the term "acute insult to the central nervous system" includes short-term events which pose a substantial threat of neuronal damage mediated by glutamate excitotoxicity. This includes ischemic events (which involve inadequate blood flow, such as a stroke or cardiac arrest), hypoxic events (involving inadequate oxygen supply, such as drowning, suffocation, or carbon monoxide poisoning), trauma to the brain or spinal cord (in the form of mechanical or similar injury), certain types of food poisoning which involve an excitotoxic poison such as domoic acid, and seizure-mediated neuronal degeneration, which includes certain types of severe epileptic seizures. It can also include trauma that occurs to another part of the body, if that trauma leads to sufficient blood loss to jeopardize blood flow to the brain (for example, as might occur following a shooting, stabbing, or automobile accident). In any of these situations, ischemic or hypoxic processes can severely aggravate the extent of excitotoxic cell death and tissue damage suffered by the CNS following the acute insult, and NMDA antagonists can help to protect the CNS against such damage (e.g., Olney 1990a; Choi 1992). Accordingly, a number of NMDA antagonists (i.e., drugs that can suppress glutamate's excitatory activity at NMDA receptors) are being studied by several major pharmaceutical companies.

In addition to neuronal damage caused by acute insults, excessive activation of glutamate receptors may also contribute to more gradual neurodegenerative processes leading to cell death in various chronic neurodegenerative diseases, including Alzheimer's disease, amyotrophic lateral sclerosis (Lou Gehrig's disease), AIDS dementia, Parkinson's disease and Huntington's chorea (Olney 1990a). It is believed by many neurologists that NMDA antagonists may someday prove useful in the therapeutic management of such chronic diseases.

Excessive activation of NMDA receptors is also responsible for the generation of "neuropathic" pain, a type of pain which is sometimes called "neurogenic pain" or "wind-up" pain (Woolf et al 1989; Kristensen et al 1992; Yamamoto and Yaksh 1992). Neuropathic pain is a chronic condition in which NMDA receptors in neural pain pathways have become "kindled" to an abnormally high level of sensitivity, so that they spontaneously convey nerve messages that the patient perceives as pain even though no painful stimulus has been inflicted. By mechanisms that are poorly understood, pathological changes associated with diabetes are conducive to the generation of neuropathic pain, a condition known as "diabetic neuropathy".

One of the distinguishing characteristics of neuropathic pain is that morphine and related pain-killing drugs which are effective in controlling other types of pain are usually ineffective in controlling neuropathic pain (Backonja 1994). Several recent reports indicate that NMDA antagonists can prevent or ameliorate neuropathic pain (Davar et al 1991; Mao et al 1992; Seltzer et al 1991; Neugebauer et al 1993; Kristensen et al 1992; Backonja et al 1994).

NMDA receptor activation has also been implicated as a mechanism underlying the development of tolerance to various potentially addictive drugs. "Tolerance" is used broadly herein, to include any or all of the following: dosage-type tolerance to a drug, which implies that a person must take an increasing amount of a drug in order to achieve the same level of sensations or therapeutic benefit; dependence upon a drug, which implies that a patient must continue taking a drug to avoid withdrawal symptoms; and, craving for a drug, which can include physiological and/or psychological cravings. A number of recent reports indicate that in animal studies, NMDA antagonists apparently prevented the development of tolerance to opiate analgesics (Marek et al 1991; Trujillo and Akil 1991; Ben-Eliyahu et al 1992; Tal and Bennett 1993) or benzodiazepine anxiolytics (L. Turski et al, PCT patent application WO 94/01094). It has also been reported that ibogaine, a drug known to have NMDA antagonist properties, can suppress the craving for cocaine (e.g., Sershen 1994).

NMDA Receptor Hypofunction (NR/hypo)

The term "NMDA receptor hypofunction" (NR/hypo) is used herein to refer to abnormally low levels of activity at NMDA receptors on CNS neurons. As discussed in the immediately following paragraphs, NR/hypo can occur as a drug-induced phenomenon, following administration of an NMDA antagonist drug such as PCP or MK-801. It can also occur as an endogenous disease process; the Applicants have discovered that NR/hypo appears to be an important mechanism responsible for symptom formation and pathological brain changes in certain neurological disorders, such as schizophrenia (and Alzheimer's disease, as discussed in detail in a separate patent application).

NR/hypo as a Drug-Induced Phenomenon: Both Beneficial and Detrimental

As described above, when NR/hypo is induced by NMDA antagonist drugs (i.e., drugs that directly suppress activity at NMDA receptors), it can have important beneficial effects in people who need protection against excitotoxic brain damage during ischemic/hypoxic crises such as stroke, cardiac arrest, or brain injury.

However, despite these potential benefits, NMDA antagonists can have serious detrimental side effects. As described in Olney et al 1989 and in U.S. Pat. No. 5,034,400 (Olney 1991), NMDA antagonists can injure and even kill neurons located in a portion of the brain known as the posterior cingulate or retrosplenial (PC/RS) cortex, and in certain other cerebrocortical and limbic regions of the animal brain.

These toxic side effects, caused by NMDA antagonists, can be evaluated and measured directly, in brain tissue from lab animals that have been sacrificed. Such tests are most commonly done on rats.

Briefly, in sacrificed animals which have been administered an NMDA antagonist drug (such as MK-801) without an accompanying safener drug, several pathological changes become fairly obvious and easily detectable in neurons located in the PC/RS cortex region of the brain. Such changes include (1) the formation of vacuoles (i.e., small bag-like sacks or organelles which are empty of the type of cellular structures that normally fill other organelles inside a cell cytoplasm; (2) mitochondrial damage or dissolution; and (3) the induction and expression of so-called "heat shock" proteins. All three of these measurable indicators (vacuole formation, mitochondrial damage, and expression of heat shock proteins) can be regarded as manifestations of serious damage to affected cells, indicating major disruption or derangement of a cell's normal structure and functioning. These cellular changes can also be correlated with behavioral abnormalities in lab animals, such as seizures, catatonic withdrawal, and abnormal responses to conventional stimuli.

In living human patients, since direct examination of brain tissue is usually not feasible prior to death, the appearance of hallucinations or other psychotomimetic symptoms (such as severe disorientation or incoherence) is regarded as a warning sign that similar types of neuronal damage may be occurring in the human brain, when NMDA antagonists are used.

Thus, a major obstacle to the use of NMDA antagonists as therapeutic drugs in humans lies in their potential for inducing toxic side effects inside the brain, including neuronal damage and even neuronal death, in certain vulnerable regions of the brain.

The Applicants herein have discovered a number of drugs that can act as "safener" drugs, to prevent NMDA antagonists from causing toxic side effects. Such safener drugs include, for example, certain anti-cholinergic drugs such as scopolamine which block activity at the m1 and m3 classes of muscarinic acetylcholine receptors, and certain types of barbiturates such as secobarbitol which act as direct agonists at GABA type A receptors. Such safener drugs are not directly relevant to the discovery of an additional safening mechanism, involving a completely different class of receptors, as disclosed herein.

Inhibitory Transmitters and Neuronal Circuits

In addition to various excitatory neurotransmitter systems, which mainly involve glutamate, acetylcholine, and neuropeptide Y, there are also several transmitter systems in the CNS that are primarily, or in some cases exclusively, inhibitory. These inhibitory systems are absolutely essential for proper functioning of the brain.

In a simplified depiction, inhibitory transmitters can be regarded as serving two distinct functions. First, they help a neuron quickly restore itself to a "resting/ready" condition, so that it will be ready to receive the next nerve signal from other neurons. And second, they help suppress or "tune out" activity caused by unwanted impulses. This is analogous to a TV or radio receiver, which cannot function properly unless it can be tuned to a single channel or station, so that it suppresses and ignores the competing signals from dozens or hundreds of other transmitting stations that may be broadcasting in the area.

Another way to understand both the importance and the mechanism of inhibitory neurotransmitters and receptors is to think in terms of gatekeepers, which establish threshold values. If a weak, low-level signal that does not reach a necessary threshold strength tries to activate a neuron, the gatekeeper will block it. However, if an incoming signal or stimulus reaches or surpasses the threshold level, the gatekeeper will let it through, and it will trigger what is, in effect, an on/off switch which controls the activation, firing, and depolarization of the neuron. This inhibitory/gatekeeping function is essential for reducing spurious and unwanted nerve cell activations in the brain, so that coherent, meaningful patterns of signals (stimuli, thoughts, memories, etc.) can be handled properly and effectively by the brain.

The predominant inhibitory transmitter in the brain is GABA (the acronym for gamma-amino butyric acid). This inhibitory transmitter has important interactions with the glutamate excitatory system in many neural circuits within the CNS. Neurons that contain and release GABA as an inhibitory transmitter are called GABAergic neurons.

Two other neurotransmitters which are mainly inhibitory inside the CNS are dopamine, and norepinephrine. Paradoxically, norepinephrine is the same peptide which, outside the CNS, is enzymatically cleaved to form epinephrine, also called adrenalin, the excitatory hormone.

Many articles and scientists also refer to serotonin as an inhibitory neurotransmitter; however, its actions are more complex. Instead of being a direct inhibitor, it actually stimulates certain neurons which then release inhibitory transmitters. Since serotonin and certain types of serotonin receptors are at the heart of this invention, they are discussed below, in a separate section.

Inhibitory/Excitatory Interactions; Disinhibition

A schematic depiction of a neuronal circuit arrangement, which can be used to help understand the neuronal mechanisms involved in this invention, is provided in FIG. 1. This depiction is based upon a combination of (1) what was previously known and reported about various excitatory and inhibitory transmitters, and (2) the Applicants' research on safening agents which can reduce the toxic side effects of NMDA antagonist drugs.

Most of the elements in this drawing, excluding the serotonin-releasing neuron 15, were published and described in olney and Farber 1995 (see FIG. 4 of that 1995 article, at page 1002). The following provides a brief summary and explanation of that circuitry, excluding neuron 15.

Under normal conditions, a "master control/driving neuron" 10 releases small, steady quantities of glutamate. This glutamate acts at NMDA receptors (indicated by asterisks in FIG. 1) on the surfaces of a number of inhibitor neurons 20 through 50. When stimulated by glutamate at their NMDA receptors, these inhibitor neurons 20–50 release inhibitory transmitters, including GABA and norepinephrine. These inhibitory transmitters then act at receptors on the surfaces of several downstream "exciter" neurons 60, 70, and 80. This imposes a restraining and inhibitory control on the exciter neurons 60–80, and it prevents them from releasing excessive quantities of their excitatory transmitters (neuropeptide Y, glutamate, and acetylcholine).

In some situations, the NMDA receptors on the surfaces of inhibitor neurons 20–50 become hypofunctional, and cannot respond properly to glutamate that is released by the master control-driving neuron 10. This can occur in at least two different types of situations. One situation occurs when NMDA antagonist drugs are administered to a lab animal or human; such drugs will interact directly with the NMDA receptors, and will block or suppress their activation by glutamate. The second situation occurs endogenously, in the brains of people suffering from certain diseases including schizophrenia. In such diseases, NMDA receptors become hypofunctional, presumably because overstimulation leads to a form of damage which can be regarded as "burnout" damage.

In either case, the condition is referred to herein as "NMDA receptor hypofunction", abbreviated as NR/hypo. When this condition occurs, the inhibitor neurons 20–50 are no longer driven to release adequate quantities of their inhibitory transmitters, and the control mechanism which normally restrains the exciter neurons 60–80 is lost or hindered.

When this condition (referred to herein as "disinhibition") occurs, the exciter neurons 60–80 begin releasing excessive quantities of their excitatory transmitters (including neuropeptide Y, or NPY, from neuron 60; glutamate, from neuron 70; and acetylcholine, from neuron 80). All of these excitatory transmitters interact with their corresponding receptors on the surfaces of a pyramidal neuron 100 in a corticolimbic region of the brain (referred to herein as a "target" neuron). If excited too heavily by excessive release of transmitters from neurons 60–80, the pyramidal neuron 100 can suffer damage or even death.

The symptoms of psychosis (including hallucinations, delusions, and other derailments or diversions of proper cognitive or mental faculties), in schizophrenics, are also believed to arise from this disinhibition process, and presumably involve the overstimulation of corticolimbic neurons, as discussed in more detail in Olney and Farber 1995.

As noted above, the foregoing analyses and neuronal circuit diagrams have been previously published (Olney and Farber 1995, in FIG. 4). The new discovery that is the foundation of this invention is the discovery that serotonin, acting through 5HT-2A receptors, is also involved in the inhibition circuitry which protects corticolimbic target neurons 100. In FIGS. 1 and 2, this involvement is represented by neuron 15, which was not shown in any prior publications; its involvement was not recognized until its recent discovery by the Applicants. Accordingly, it is part of this invention rather than background or prior art, and it is discussed below.

Before the involvement of 5HT-2A agonist drugs in this invention can be understood, background information on serotonin and the "serotonergic" receptor system is necessary.

The Serotonin Transmitter/Receptor System

This section briefly provides background information on the serotonin transmitter and receptor system. More information is provided in various medical textbooks on neurology, including the chapter by Aghajanian, in the *Encyclopedia of Neuroscience*, edited by Adelman (1987); the chapter by Frazer and Hensler, in *Basic Neurochemistry*, edited by Siegel et al (1994); and chapters 36 through 42 of *Psychopharmacology*, edited by Bloom and Kupfer (1995).

Briefly, serotonin is the common name for a chemical called 5-hydroxytryptophan (abbreviated as 5HT). This neurotransmitter is synthesized and secreted primarily by certain large neurons clustered in several groups (B1 through B9) in the "raphe" region of the midbrain and brainstem. Neurons in groups B6 through B9 send long axonal processes to many regions of the forebrain, including the cerebral cortex, where these axons contact various neurons in the forebrain. Acting through these long axonal processes, the B6–B9 neurons which originate in the midbrain release serotonin into the forebrain.

Neuronal receptors which are triggered by serotonin are called serotonergic or 5HT receptors. These receptors are (currently) divided into seven classes, designated as 5HT-1, 5HT-2, etc., up to 5HT-7 (Zifa and Fillion, 1992; Martin and Humphrey, 1994). Some of these classes are further subdivided; class 1 is divided into 1A, 1B, 1D, 1E, and 1F. Class 2 is divided into 2A, 2B, and 2C.

During the late 1980's and early 1990's, there were several changes in serotonin receptor designations, to reflect recent discoveries and refinements. Receptors that were previously referred to as "5HT-2 receptors" are now called 5HT-2A receptors, and receptors that previously were called 5HT-1C receptors are now called 5HT-2C receptors. The designation "5HT-1C" was retired when it was discovered that those receptors belonged in class 2 instead.

In the 5HT-2 family of receptors, only the 2A and 2C subclasses are found in the central nervous system, and thus are of interest herein.

Serotonin is often called an inhibitory neurotransmitter. This is its net effect, but it should be recognized that serotonin usually exerts this net effect by stimulating GABA-releasing neurons to release GABA, which is a true inhibitory transmitter. Accordingly, serotonin actually excites neurons, via 5HT-2A receptors, but those neurons then release inhibitory transmitters which suppress "downstream" activity in the brain.

Serotonin (the natural neurotransmitter) activates all subtypes of 5HT receptors. In contrast, several selective agonists or partial agonists have been discovered which selectively activate 5HT-2A and 5HT-2C receptors with higher affinity than other 5HT receptors. These agents include DOM (which stands for 1-(2,5-dimethoxy-4-methylphenyl)-2-aminopropane), DOI (which stands for 1-(2,5-dimethoxy-4-iodophenyl)-2-aminopropane, and DOB (which stands for 1-(2,5-dimethoxy-4-bromophenyl)-2-aminopropane). The famous hallucinogen LSD (lysergic acid diethylamide) also agonizes 5HT-2A and 5HT-2C receptors, and possibly other serotonin receptors as well.

None of these drugs can be used legally by humans in the United States; they all cause hallucinations, so they were classified by the Food and Drug Administration as "Schedule 1" drugs, to reduce their supply and circulation, and their potential risks of illegal abuse. In addition to hallucinations, these drugs also cause a variety of other symptoms that can be studied and measured in lab animals, including decreased pain, muscle twitching, changes in temperature regulation and sleep patterns, changes in sexual behavior, and other changes in behavior that appear to be related to anxiety and depression.

These agonists all stimulate activity with both 5HT-2A and 5HT-2C receptors, and it has not been established which receptors are responsible for any of the effects listed above. The extent to which these drugs interact with other non-serotonin receptor systems is not fully understood.

Serotonin and Schizophrenia

A potentially significant role for the serotonin system in schizophrenia has been suspected since the discovery that the hallucinogen LSD acts at serotonin receptors, and numerous investigators have documented changes in levels of serotonin and its major metabolite (5-hydroxy-indoleacetic acid) in the cerebrospinal fluid of schizophrenic patients. Several non-selective serotonergic agonists (including fenfluramine, m-chlorophenylpiperazine (mCPP) and tryptophan) can exacerbate the symptoms and displays of schizophrenia, and the exacerbation by mCPP can be blocked by a 5HT-2A/2C antagonist, ritanserin. This has led some researchers to conclude that overactivity of one or both of these two receptors could account for some of the symptoms of schizophrenia, and that antagonists of these receptors could be useful therapeutic agents.

Clozapine, a relatively new anti-psychotic agent which is commonly called an "atypical" anti-psychotic, to distinguish it from various older anti-psychotic drugs, has been shown to be more effective than the older anti-psychotic drugs in treating many schizophrenics. It has a high affinity for several serotonin receptors (5HT-2A, 5HT-2C, 5HT-3, 5HT-6, and 5HT-7. Analysis of the binding affinities of clozapine (and several other presumed atypical anti-psychotic drugs) for several serotonergic receptors has led a number of eminent authorities in schizophrenia research to conclude that antagonism (not agonism) at the 5HT-2A receptor appears to be the critical action responsible for clozapine's therapeutic efficacy; a review is presented in Chapter 102 of

Psychopharmacology: The Fourth Generation of Progress.

Based on this line of research (which, it should be noted, teaches directly away from the subject invention), various drugs have been developed which selectively block (antagonize) action at 5HT-2A and/or 5HT-2C receptors, and some of these blocking drugs have been used to treat schizophrenia in humans. Methysergide, setoperone, ritanserin, melperone, amperozide were all evaluated in humans for antipsychotic activity (Bersani et al 1986; Gelders et al 1985; Reyntjens et al 1986; Bjerkenstet 1989; Ceulemans et al 1985; Gustafson and Christensen 1990; Leysen et al 1985; Mendels et al 1967; Ohuoha et al 1993; also see Nozulak et al 1993, regarding SDZ SER 082). Only ritanserin showed sufficient efficacy to justify ongoing human clinical research; it also reportedly could help reduce the incidence of certain "extrapyramidal" side-effects (manifested by problems with muscle control) caused by certain other antipsychotic agents like haloperidol.

However, ritanserin only helped relieve certain "negative" symptoms of schizophrenia (this refers to symptoms or behavior that indicate the absence of a normal response; it includes emotional withdrawal, blunted affect, autism, avolition, or anhedonia, when such displays extend beyond the normal ranges displayed by competent adults). It did not help relieve "positive" symptoms, which includes auditory, tactile, or visual hallucinations, and delusions.

To the best of the Applicants' knowledge and belief, the manufacturers of ritanseran and all other 5HT-2A/2C antagonist drugs have stopped selling them for human use and have withdrawn them from clinical development, because of a combination of adverse side effects coupled with their inability to treat positive symptoms. However, a more selective drug called MDL 100,907, which preferentially antagonizes 2A receptors and does not substantially affect 2C receptors, reportedly is still being evaluated (Schmidt et al 1995; also see Fiorella et al 1995a, Kuoppamaki et al 1995; Kehne et al 1996).

In addition, some 5HT receptors (probably those in the 5HT-1 family) apparently have an auto-regulating function, comparable to a feedback loop; when activated by serotonin, these receptors apparently act to suppress the release of additional serotonin.

To the best of the Applicants' knowledge and belief, nothing in the prior art discloses or suggests the use or the ability of a 5HT-2A agonist to block the neurotoxic side effects of an NMDA antagonist. It was not previously recognized that the 5HT-2A receptor system has an inhibitory effect on neurons involved in the neurotoxic side effects caused by NMDA antagonists and by NMDA receptor hypofunction.

In addition, to the best of the Applicants' knowledge and belief, nothing in the prior art discloses or suggests that use of 5HT-2A agonists might be useful in the treatment of schizophrenia. Indeed, in view of the fact that 5HT-2A/2C blockers (antagonists) such as ritanserin have been considered useful for treating schizophrenia, the prior art apparently teaches away from the use of 5HT-2A agonists, which have the opposite effect at the relevant receptors and which presumably would aggravate rather than treat schizophrenia.

Accordingly, the involvement of the 5HT-2A receptor system in reducing or preventing the toxic side effects of NMDA receptor hypofunction (NR/hypo) is regarded as part of the subject invention.

In addition, based on several recent discoveries discussed below, it appears that the neurotoxic condition referred to herein as NR/hypo occurs, not just in people taking NMDA antagonist drugs, but also as a natural process in certain types of diseases, including (apparently) schizophrenia and Alzheimer's disease, which are two of the most devastating and intractable mental diseases known to humankind. Accordingly, it is believed by the Applicants that drugs which can prevent the toxic side effects of NMDA antagonists may also be able to help prevent or retard the progressive brain damage that is occurring naturally in the brains of people suffering from schizophrenia or Alzheimer's disease.

Despite the discovery of various types of safening agents which can be used to reduce the toxic side effects of NMDA antagonists (such as anti-cholinergic drugs, thiobarbiturates, etc.), there remains a need for improved treatments which take advantage of the potential beneficial effects of NMDA antagonists, while avoiding their toxic side effects. That type of improved treatment, using drugs which act as agonists at 5HT-2A receptors inside the brain, is one of the objects and disclosures of this invention.

There is also a huge and extremely important medical and social need for improved treatments that can prevent, or at least reduce the damage and the symptoms of, schizophrenia and/or Alzheimer's disease.

Accordingly, one object of this invention is to disclose that treatment using drugs which act as agonists at 5HT-2A receptors, inside the brain, can prevent or reduce the toxic side effects of NMDA antagonist drugs, including both (1) various drugs which are illegally abused, such as phencyclidine ("angel dust"), and (2) drugs which are administered by physicians to reduce excitotoxic damage, either during or after a crisis such as a stroke or to treat a progressive neurodegenerative disease, or to ameliorate neuropathic pain or prevent tolerance or addition to opioid analgesics.

Another object of this invention is to disclose that drugs which act as agonists at 5HT-2A receptors, inside the brain, can be used to prevent or reduce the neurological damage and symptoms of schizophrenia.

Another object of this invention is to disclose that drugs which act as agonists at 5HT-2A receptors, inside the brain, can be used to prevent or reduce the neurological damage and symptoms of Alzheimer's disease.

SUMMARY OF THE INVENTION

This invention relates to a new method for treating or preventing brain damage caused by NMDA receptor hypofunction (NR/hypo), using drugs such as lisuride which stimulate (agonize) activity at the 5HT-2A class of serotonin receptors, but which do not cause hallucinations. Data disclosed herein indicate that stimulation of both 5HT-2A and 5HT-2C receptors causes hallucinations, while stimulation of 5HT-2A receptors but not 5HT-2C receptors does not. Accordingly, to be useful herein, non-hallucinatory 5HT-2A agonists should either (1) antagonize (suppress) activity at 5HT-2C receptors, or (2) have no significant effect on activity at 5HT-2C receptors. Selective non-hallucinatory 5HT-2A agonists can be used in either of two treatment methods disclosed herein.

One such treatment comprises administering a 5HT-2A receptor agonist as a "safener drug" which accompanies an NMDA antagonist drug that is being used for a therapeutic purpose. There are at least four situations where NMDA antagonist drugs offer major promise of benefit: (1) reducing excitotoxic brain damage during or after an ischemic or hypoxic crisis, such as stroke, cardiac arrest, or near-suffocation; (2) treating certain neurodegenerative diseases in which excitotoxic damage plays a role; (3) reducing neuropathic pain; and, (4) preventing or reducing tolerance and addiction to various types of drugs such as morphine. In such situations, the NMDA antagonist drug can exert a primary beneficial effect, and the 5HT-2A agonist drug will act as a "safener" drug to prevent certain types of toxic side effects that would be caused by an NMDA antagonist drug in the absence of a safener drug.

Another method disclosed herein involves the use of a 5HT-2A agonist drug, by itself, to combat a naturally-occurring form of NMDA receptor hypofunction which occurs in people suffering from schizophrenia. Although 5HT-2A agonists would not be optimally effective in treating long-standing cases of chronic schizophrenia, where pathological changes in the brain have already reached maximal or severe levels, 5HT-2A agonists can be administered early in the illness, such as at the first signs of schizophrenic illness, and continuously thereafter to prevent the development or worsening of pathological brain dysfunction and the resulting psychosis.

DESCRIPTION OF THE PREFERRED EMBODIMENTS

It has been discovered by the Applicants that 5HT-2A receptors are critically involved in the neuronal circuitry which mediates certain adverse CNS effects caused by NMDA receptor hypofunction (NR/hypo). Accordingly, this invention discloses a method for treating (this term is used broadly, to include preventive as well as therapeutic treatment) adverse CNS effects produced by NR/hypo. This method comprises administering, to a human or other mammalian patient, a 5HT-2A agonist drug (which includes pharmacologically acceptable salts of such drugs), in an amount effective for inhibiting the adverse CNS effects produced by NR/hypo.

In one embodiment of this method, drugs (such as lisuride) which activate and stimulate activity at 5HT-2A receptors but which do not cause hallucinations can be co-administered with NMDA antagonists to reduce the toxic side effects of NMDA antagonists, without blocking the beneficial primary effects of NMDA antagonists. This allows the use of such drug combinations (i.e., a 5HT-2A agonist, and an NMDA antagonist) to be used for any of several therapeutic purposes, including: (1) prevention of neuronal degeneration associated with acute CNS injury syndromes, including hypoxia/ischemia (stroke), cardiac arrest, asphyxia, CNS trauma or other trauma involving loss of blood, and major epileptic seizures; (2) prevention of gradual excitotoxic neuronal degeneration which may accompany various progressive degenerative diseases, such as Alzheimer's disease, amyotrophic lateral sclerosis, AIDS dementia, Parkinson's disease, and Huntington's chorea; (3) alleviation of chronic neuropathic pain; and, (4) prevention of tolerance or addictive responses to certain types of potentially addictive drugs, including opiates, sedatives, anxiolytics, and possibly cocaine.

In another embodiment of this invention, 5HT-2A receptor agonists which do not cause hallucinations can be used to treat schizophrenia. By preventing endogenously-occurring NMDA receptor hypofunction (NR/hypo) from leading to excitotoxic damage to pyramidal and other corticolimbic neurons (via the disinhibition process discussed above), 5HT-2A receptor agonists can help prevent, reduce, or retard the progressive neurodegeneration that occurs in schizophrenic patients.

These uses are discussed in more detail below.

Discovery of 5HT-2A Receptors in Inhibition Circuit

Figure 1:
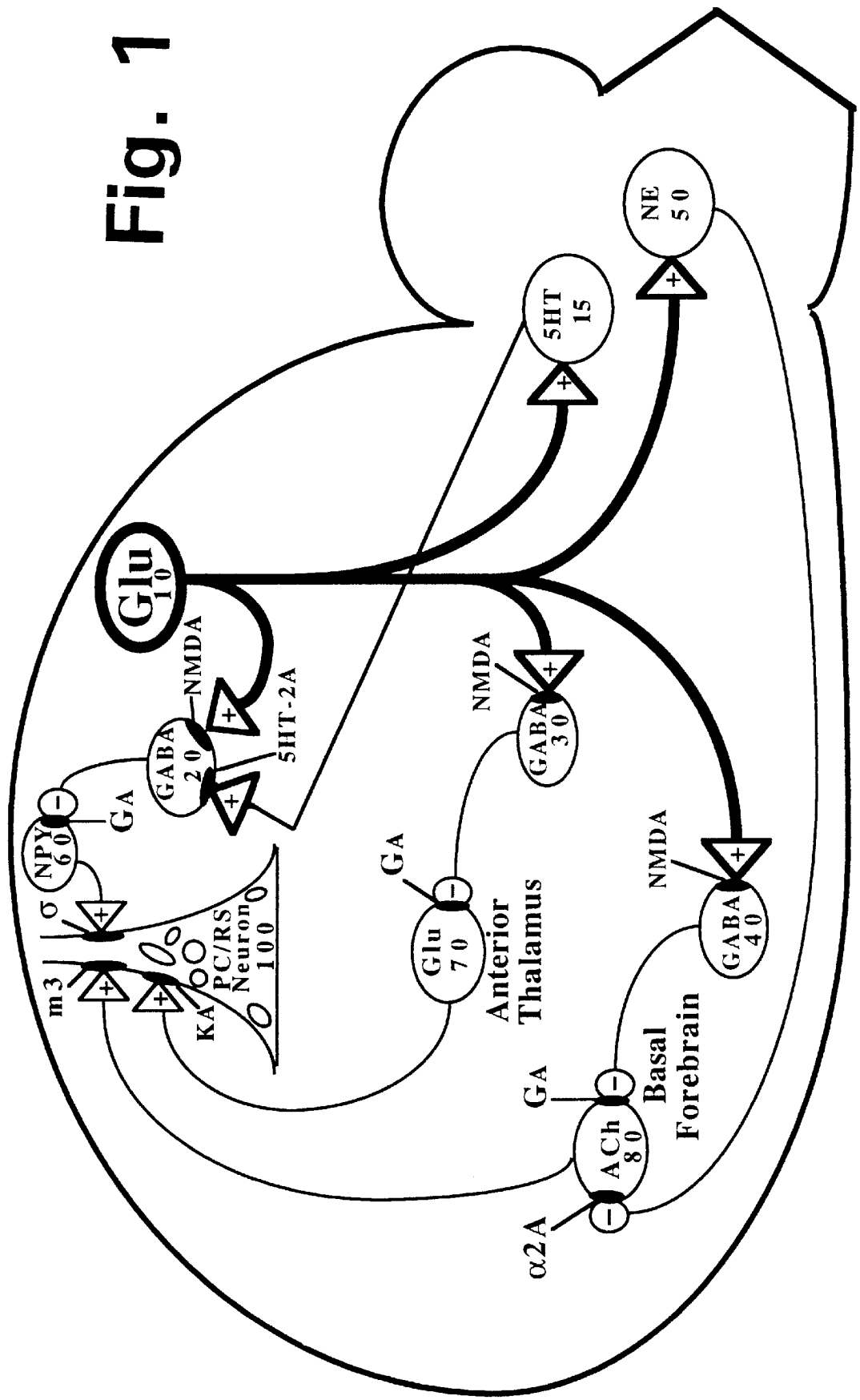
FIG. 1 is a schematic depiction of a neural circuit in a healthy brain. Most of this circuit has been previously published; the only new element involves serotonin release by neuron 15, which acts at a 5HT-2A receptor on neuron 20. In this circuit, a glutamate-releasing neuron 10 stimulates various neurons (including neuron 15) to release inhibitory neurotransmitters. These inhibitory neurotransmitters act at other downstream exciter neurons, in a manner that protects a pyramidal neuron in the posterior cingulate or retrosplenial (PC/RS) cortex against toxic overstimulation.
Figure 2:
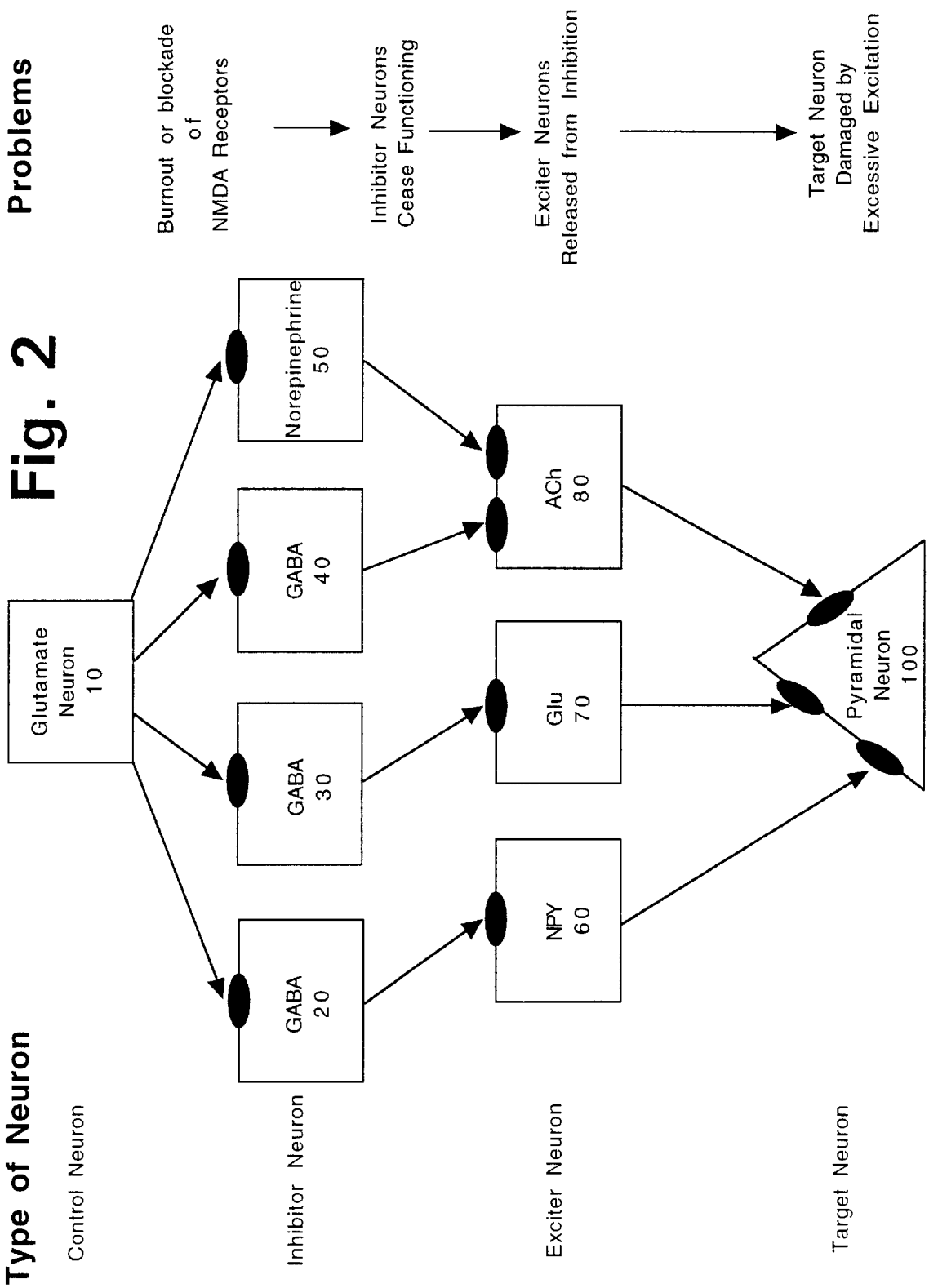
FIG. 2 is a schematic depiction of a neural circuit in a brain that is suffering from NMDA receptor hypofunction (NR/hypo), in which the master driving neuron 10 can no longer adequately stimulate the inhibitor-releasing neurons.

As noted above, most of the neuronal and transmitter elements shown in FIGS. 1 and 2 were previously published, in FIG. 4 of Olney and Farber 1995.

The foundation of this invention is the recent discovery that serotonin, acting through 5HT-2A receptors, is also involved in the inhibition circuitry which protects corticolimbic target neurons 100. This involvement is represented, in FIGS. 1 and 2, by neuron 15, which was not shown in any prior publications.

In FIG. 2, serotonin-releasing neuron 15 is referred to as an "accessory driving neuron". This is because it does not directly inhibit any of the exciter neurons 60–80. Instead, the release of serotonin by neuron 15 activates one or more of the inhibitor neurons 20–50, by means of activating 5HT-2A receptors. This activation stimulates the inhibitor neuron(s), which in turn causes and drives them to release their inhibitory transmitters, such as GABA or norepinephrine.

NMDA receptor hypofunction (NR/hypo) can be caused either (1) by administering NMDA antagonist drugs, or (2) by a disease process that occurs naturally in schizophrenia and possibly certain other neuronal diseases. Regardless of how it begins, it can suppress and prevent the activation of serotonin-releasing neuron 15. This, in turn, interferes with the control system that normally protects pyramidal neurons 100 in healthy brains.

Accordingly, neuronal problems that are caused or mediated by a NR/hypo condition inside the brain can be treated by administering a 5HT-2A agonist drug. By activating inhibitory neurons, such as neurons 20–50 in FIGS. 1 and 2, the 5HT-2A agonist drug can restore inhibitory control over one or more of the exciter neurons 60–80, and can prevent those exciter neurons from overstimulating and injuring corticolimbic target neurons 100.

Accordingly, a 5HT-2A agonist drug provides a pharmaceutical means for bypassing a silenced serotonin-releasing neuron 15, and reinstating the inhibitory mechanism which protects corticolimbic neurons, such as pyramidal neuron 100, against toxic overstimulation.

Evaluation of Various 5HT-2A Agonists

As mentioned above, although there are serotonergic agonists which act preferentially at the 5HT-2 family of receptors over other 5HT receptors (including LSD, DOI, DOM, and DOB; their full chemical names are listed above), they are not in clinical use because of their hallucinogenic action. While the 5HT-2 receptor system has been implicated in the hallucinogenic activity of these drugs, the precise receptor subtype(s) responsible for hallucinations caused by these drugs has remained elusive. Most investigators apparently have assumed or concluded that agonist action at the 5HT-2A receptor is critical for hallucinations (Titeler et al 1988; Fiorella et al 1995b and 1995c); however, other reports suggest that agonism of the 5HT-2C receptor probably accounts for, or at least contributes to, the hallucinogenic action of these drugs (Burris et al 1991).

Based on their recent research, especially tests involving lisuride (a non-hallucinogenic 5HT-2A agonist) it is believed by the Applicants that the hallucinatory effects of these drugs are due to either (1) agonist activity at the 5HT2C class of receptors, or (2) combined activity at both 5HT-2C and 5HT-2A receptors.

Lisuride agonizes 5HT-2A receptors, but has the opposite effect (i.e., antagonism and suppression of activity) at 5HT2C receptors (Burris et al 1991). It does not cause hallucinations, and it is approved for human use in Europe as a treatment for migraine headaches, under trademarks such as Cuvalit, Dopergin, Eunal, and Lysenyl. It is also a prolactin inhibitor (prescribed for women who want to stop lactating, after nursing a baby), and is used to treat Parkinson's disease. It is described in *The Merck Index*, and in various publications cited therein.

Lisuride is also an agonist at the D2 class of dopamine receptors. If it is used to treat schizophrenics, this D2 dopamine activity raises concerns, since it might cause side effects which would need to be carefully evaluated. However, these side effects might be resolved by co-administering a D2 antagonist along with lisuride.

It is also suspected that one of the stereoisomers of lisuride may have a high level of agonist activity at 5HT-2A receptors, and a low level of agonist activity at D2 receptors; this will be evaluated, and if it turns out to be the case, that stereoisomer of lisuride would be a preferred agent for treating schizophrenia, and possibly for other uses to reduce or prevent the side effects of NMDA receptor hypofunction (NR/hypo).

Isomers and analogs of lisuride also offer good candidates for development and use as described herein, provided that (1) they must not cause hallucinations, and (2) they must agonize activity at 5HT-2A receptors, while either suppressing activity or causing no significant activity at 5HT-2C receptors. Preferably, such analogs should also have either little or no activity, or mild antagonistic activity, at D2 dopamine receptors.

Accordingly, lisuride is believed to be suitable, in its currently available form, to reduce or prevent the side effects of at least some types of NMDA receptor hypofunction (NR/hypo), in humans. In addition, it is believed to have some utility in its current form for treating at least some schizophrenics, and it provides a promising starting point for developing related isomers and analogs which would have even better efficacy, through better and more selective agonist activity at 5HT-2A receptors coupled with lower activity at dopamine D2 receptors.

The Applicants have also commenced a program of searching for other published reports in the scientific and medical literature which suggest that various other drugs may be 5HT-2A agonists which do not have 5HT-2C agonist activity. Any such drugs will be evaluated to carefully assess their activities at 5HT-2A, 5HT-2C, and dopamine receptors, to determine whether they may be useful for suppressing the toxic side effects of NMDA receptor hypofunction and for treating schizophrenia.

In addition, the disclosure herein of two valuable uses for drugs which agonize activity at 5HT-2A receptors, but which do not also trigger activity at 5HT-2C receptors, is likely to provoke pharmaceutical companies to test their company "libraries" of compounds (both commercial and non-commercial compounds), to determine whether any such compounds have the desired combination of 5HT-2A agonist activity coupled with either (a) no activity at 5HT-2C receptors, or (b) some antagonist activity at 5HT-2C receptors.

Use of 5HT-2A Agonists and NMDA Antagonists to Treat Excitotoxicity

As mentioned above, it is disclosed herein that a 5HT-2A agonist drug can act as a safener agent, for co-administration with an NMDA antagonist drug, to prevent or reduce the toxic side effects of the NMDA antagonist.

The tests which revealed this safening activity are described in more detail in Examples 1 and 2. Briefly, rats were injected with MK-801, a powerful, highly selective, and relatively long-lasting NMDA antagonist. Each test rat also received a 5HT-2A/2C agonist drug (LSD, DOB, DOI, or DOM), while control rats received an inert carrier liquid as a placebo. After 4 hours, the rats were sacrificed, and brain tissue from specific regions which are susceptible to NR/hypo damage (layers III and IV of the posterior cingulate (PC) and retrosplenial (RS) cortices) were examined for vacuoles in the neurons, which are an indicator of toxic neuronal injury induced by NMDA receptor hypofunction.

The results, in Table 1, indicated that a prominent vacuole reaction occurred in all animals that received the MK-801 alone. However, in animals which also received a 5HT-2A/2C agonist drug, the 5HT-2A/2C agonist drug was effective in preventing the formation of vacuoles.

The drug lisuride is treated separately in the Examples, because it has a different set of receptor activities; it is a 5HT-2A agonist, but it is also a 5HT-2C antagonist. As described in Example 3, it can prevent vacuole formation caused by MK-801.

As described in Example 4, it was also shown that 5HT-2A/C agonists do not interfere with the useful beneficial effects of MK-801, in protecting neurons against excitotoxic damage caused by ischemia/hypoxia.

Accordingly, a 5HT-2A agonist which does not cause hallucinations can be co-administered with an NMDA antagonist drug, to allow the NMDA antagonist drug to exert a primary benefit, while the 5HT-2A agonist prevents or reduces the toxic side effects that would be caused by the NMDA antagonist in the absence of a safener drug.

One important potential use for NMDA antagonist drugs involves their ability to prevent or reduce excitotoxic damage to neurons. Excitotoxic damage can occur as a result of an acute insult to the patient's central nervous system, such as a stroke, cardiac arrest, physical injury, near-suffocation, carbon monoxide poisoning, edematous swelling, or other trauma or insult which blocks or impedes blood flow through, or oxygen supply to, the brain. Excitotoxic damage is also believed to play a contibutory role in a number of progressive neurodegenerative disease, including amyotrophic lateral sclerosis (Lou Gehrig's disease), AIDS dementia, Parkinson's disease and Huntington's chorea (Olney 1990a). NMDA antagonists are being intensively studied by numerous drug companies, and they hold great promise for treating each of these classes of problems. Accordingly, this invention discloses a new class of safener agents which allows NMDA antagonist drugs to be used safely in treating acute insults to the brain, and in treating progressive neurodegenerative diseases which involve an excitotoxic component.

In addition, the Applicants have recently discovered a number of correlations between NMDA receptor hypofunction, and Alzheimer's disease. These correlations suggest that safener drugs which can block the toxic side effects of NMDA antagonists can also prevent or reduce certain types of neurodegeneration caused by Alzheimer's disease. NMDA antagonist drugs may be useful for treating Alzheimer's disease, but only during the very early stages of the disease (such as before outward symptoms begin to be displayed, indicating a substantial degree of internal neuronal damage). The use of such NMDA antagonist drugs should be discontinued after symptoms of Alzheimer's disease begin to be displayed by a patient. However, administration of one or more safener drugs should be continued even after symptoms are displayed, and presumably for the entire remaining life of the patient.

This stage-dependent form of treatment for Alzheimer's disease is discussed in more detail in a separate patent application, filed by the same Applicants herein. 5HT-2A agonists which do not cause hallucinations are believed by the Applicants to be suitable for such use in treating Alzheimer's disease.

Treatment of Neuropathic Pain

Several published reports have stated that NMDA antagonists may be effective in alleviating neuropathic pain (e.g., Davar et al 1991); by contrast, most other analgesics (including opiates, such as morphine) are ineffective in suppressing this type of pain. Therefore, it would be highly desirable and useful to have a safe method of using NMDA antagonists to prevent and reduce neuropathic pain, without risking the toxic side effects of NMDA antagonists. Accordingly, combined treatment with both an NMDA antagonist (as a primary pain-control agent) and a 5HT-2A agonist (as a safener agent, to prevent the toxic side effects of the NMDA antagonist) can satisfy an important need in the clinical management of neuropathic pain.

Avoidance of Tolerance and Addiction

In most cases of chronic pain other than neuropathic pain, opiate analgesics are initially very effective in alleviating the pain, but the patient rapidly develops tolerance to the opiate, so that an escalation of the opiate dosage is required to keep the pain under control. This can lead to physical dependence upon, and addiction to, the opiate.

In a new type of chronic pain treatment disclosed herein, three different drugs are used. A relatively low dosage of an opiate analgesic is administered, to treat the chronic pain. An NMDA antagonist is also administered, to prevent or reduce the development of tolerance or addiction to the opiate analgesic. As the third component, a 5HT-2A agonist drug is also administered, to prevent any neurotoxic side effects from being caused by the NMDA antagonist.

Accordingly, this invention discloses a mixture, comprising: (1) an opiate analgesic, at a dosage which helps control chronic pain; (2) an NMDA antagonist, at a dosage which reduces the development of tolerance or addiction to the opiate analgesic; and, (3) a 5HT-2A agonist drug, at a dosage which prevents any neurotoxic side effects from being caused by the NMDA antagonist. This invention also discloses a method of treating chronic pain, by means of administering all three drugs to a patient, either in a mixture or by means of overlapping regimens, so that all three drugs can exert their effects simultaneously.

Treatment of Schizophrenia

When a condition of NMDA receptor hypofunction (NR/hypo) is induced in the brain by an NMDA antagonist drug, the disinhibition process results in psychosis in humans, and neuropathological changes in corticolimbic brain regions in the rat. These neuropathological changes cause permanent deficits in cognitive function (Brosnan-Watters et al 1994). Psychosis, neuropathological changes in corticolimbic brain regions, and cognitive deterioration, are all hallmark characteristics of schizophrenia (reviewed in Olney and Farber 1995).

Because of certain similarities between the mental and behavioral aberrations and pathological brain changes caused by NMDA antagonist drugs, and the mental and behavioral aberrations and pathological brain changes observed in schizophrenia, some neurologists (but not all, by any means) have suspected for years that there may be some correlation between NMDA receptor dysfunction, and schizophrenia. Examples of items which proposed such a link include Javitt and Zukin 1991, Krystal et al 1994, and the chapter by Bunney et al in *Psychopharmacology* (edited by Bloom and Kupfer 1995). None of those articles were able to establish and demonstrate any causative mechanisms or neuronal circuitry to confirm that hypothesis.

The Applicants' recent research described herein has elucidated several aspects of the neural circuitry which appears to underlie the mental and behavioral aberrations and pathological changes that seem to occur when NMDA receptors are rendered dysfunctional, and it has offered a plausible and apparently consistent explanation of what happens when NMDA receptor hypofunction (NR/hypo) occurs inside the brain.

Accordingly, this description and the neural circuitry that is depicted herein are offered by the Applicants as an apparent explanation for the similarities that exist between the mental and behavioral aberrations and pathological brain damage caused by drug-induced NR/hypo, and the mental and behavioral aberrations and pathological brain damage that occur in schizophrenics. It is believed and asserted by the Applicants that NR/hypo is an important causative mechanism in schizophrenia. Regardless of whether it is the sole causative mechanism, or is merely responsible for only some manifestations or aggravation of the disease, it nevertheless appears to play an important role in the brain damage and mental aberrations that occur in schizophrenics.

It is also asserted by the Applicants that drugs which can block the neuronal damage caused by NMDA antagonist drugs (i.e., drugs which chemically induce an artificial condition of NR/hypo in the brain) can also block the neuronal damage caused by a similar, but naturally occurring, NR/hypo condition in the brains of at least some schizophrenics. Accordingly, this invention discloses a method for treating schizophrenia, to halt its progression and prevent it from becoming worse, by administering a pharmacologically acceptable 5HT-2A agonist drug which does not cause hallucinations.

Preferably, the administration of a 5HT-2A agonist drug as disclosed herein should begin in a timely manner, as soon as practical after the onset of symptoms of schizophrenia. This can help prevent the NR/hypo mechanism from causing subsequent pathological damage to the corticolimbic neurons that are vulnerable when a NR/hypo condition renders the protective inhibitory control system inoperative. However, even in subsequent stages of the disease, after a substantial degree of damage to vulnerable pyramidal and other corticolimbic neurons has already occurred, administration of a 5HT-2A agonist drug may still be useful and beneficial, to avoid additional neuronal damage that would make the disease even worse.

It is also anticipated that in many and perhaps most patients, long-term maintenance-type treatment, using oral or slow-release formulations on a precautionary basis, will be preferred, to avoid or minimize the risk of worsening of the mental aberrations and pathological brain changes that occur in the absence of maintenance therapy. However, in other patients, intermittent or episodic treatment may be preferred, such as during periods of stress at work or home.

Drug Mixtures

One preferred composition of matter of this invention comprises a pharmacologically acceptable 5HT-2A agonist drug in a formulation and dosage that can be administered on its own (i.e., as a stand-alone agent, without an accompanying NMDA antagonist drug). This composition can protect against damage caused by naturally-occurring NMDA receptor hypofunction (NR/hypo), as occurs in schizophrenia.

A second preferred composition of matter of this invention comprises a pharmacologically acceptable mixture of (1) an NMDA antagonist drug, in a dosage that can prevent or reduce excitotoxic brain damage following an acute insult to the CNS, such as an ischemic or hypoxic crisis (stroke, cardiac arrest, brain trauma, blood loss, near-asphyxiation, carbon monoxide poisoning, etc.); (2) a 5HT-2A agonist drug; and (3) a carrier substance, such as a liquid diluent that renders the mixture suitable for intravenous injection. For this type of use, the dosage of the NMDA antagonist drug will be relatively high; this mixture will be intended only for use in short-term, acute care situations. The 5HT-2A agonist drug should be present in a dosage that can prevent any neurotoxic side effects of the high-dosage NMDA antagonist drug.

A third preferred composition of matter of this invention comprises a pharmacologically acceptable mixture of (1) an NMDA receptor antagonist drug, in a low dosage that is intended for repeated, long-term use; (2) a 5HT-2A agonist drug; and, (3) a carrier substance, such as a binding agent that allows the NMDA antagonist and the 5HT-2A agonist to be combined in a tablet or capsule form that can be swallowed rather than injected. In such long-term uses, the NMDA antagonist drug is present in a dosage that can help (a) alleviate neuropathic pain; (b) avoid a tolerance or addictive response to an opiate drug; or (c) prevent excitotoxic damage due to a progressive neurodegenerative disease. For this type of use, the dosage of the NMDA antagonist drug will be relatively low, and the 5HT-2A agonist drug can also be present in a correspondingly low dosage.

A fourth preferred composition of matter of this invention comprises a pharmacologically acceptable mixture of (1) an opiate analgesic drug, in a dosage intended for treating a chronic pain condition; (2) an NMDA receptor antagonist drug, in a dosage that is effective in reducing tolerance or addiction to the opiate analgesic; (3) a 5HT-2A agonist drug, in a dosage which can inhibit the adverse neurological effects that would be caused by the NMDA antagonist drug in the absence of the 5HT-2A agonist drug; and, (4) a carrier substance, such as a binding agent that allows the entire mixture to be combined in a tablet or capsule form that can be swallowed.

As used herein, the phrase "pharmacologically acceptable" refers to drugs (and drug mixtures as disclosed above) which satisfies all of the conventional pharmaceutical criteria (e.g., the drug or mixture must be non-toxic, non-carcinogenic, and suitable for oral ingestion, hypodermic injection, or other conventional administration, and it also must have sufficient chemical stability to allow shipping, storage, handling, and administration without requiring extreme measures). In addition, the drug or mixture must not cause hallucinations or other substantial impairments of cognitive or mental processes and capabilities in humans.

In addition to all of the foregoing criteria, any 5HT-2A agonist or NMDA antagonist must be capable of permeating a mammalian blood-brain barrier (BBB) in sufficient quantities to exert a therapeutic effect as described herein. The relevant receptor activities all occur inside CNS tissue, in extracellular fluids that are isolated from circulating blood by the BBB.

It should also be noted that the drugs disclosed herein might be usefully combined with various other drugs, for treatment of certain patients. For example, if lisuride or some other agent which has some agonist activity at dopamine receptors is used, it can be co-administered with a dopamine D2 antagonist such as haloperidol, or a dopamine D4 antagonist such as clozapine, to suppress any unwanted side effects that might be caused or aggravated by the dopamine-stimulating actions of the lisuride or other 5HT-2A agent.

In addition, the Applicants have previously reported that various other classes of drugs (including drugs which suppress activity at muscarinic, sigma, or kainic acid receptors, and drugs which increase activity at alpha-2 adrenergic or GABA type A receptors) are also effective as safening agents which can prevent the neurotoxic side effects of NMDA antagonist drugs such as MK-801 and PCP. Accordingly, it may be useful to co-administer a 5HT-2A agonist as disclosed herein, with one of those additional agents. This combined treatment might help ensure a high level of protection for vulnerable pyramidal and other corticolimbic neurons. This may be especially useful in patients suffering from relatively advanced schizophrenia or Alzheimer's disease; such patients have already suffered substantial and clearly evident neuronal damage, and they presumably are suffering from relatively extensive NMDA receptor burnout damage, which poses a constant risk of additional damage to the corticolimbic neurons. Combined treatments involving two or more different types of safener drugs which act at different receptor types might also allow each safener drug to be used in small and sparing quantities, thereby sustaining a better overall balance of undiminished receptor activities and possibly causing fewer undesirable side effects.

Dosages and Modes of Administration

The administration of 5HT-2A agonist drugs (and NMDA antagonists, and opiate analgesics, in certain mixtures) as described herein will be done under the supervision of a treating physician. These drugs are for prescription use only, and over-the-counter availability is not anticipated or intended.

The preferred dosage and mode of administration of a 5HT-2A agonist for preventing NR/hypo-related neuronal damage will vary for different patients, depending upon factors that will need to be individually reviewed by the treating physician. For example, if a 5HT-2A agonist is co-administered as a safening agent along with an NMDA antagonist that is being used to prevent excitotoxic brain damage, or to treat neuropathic pain or as an adjunct with an opiate drug to prevent tolerance or addition to the opiate drug, the relevant factors will include: (1) the potency and dosage of the NMDA antagonist being used; (2) the abilities of the NMDA antagonist and the 5HT-2A agonist to penetrate the blood-brain barrier; (3) the severity of the neurotoxic side effects produced by that particular NMDA antagonist, in the absence of a safening agent; and, (4) whether the 5HT-2A agonist is being administered before, after, or simultaneously with the NMDA antagonist.

As a general rule, the quantity of a 5HT-2A agonist which should be co-administered with an NMDA antagonist is the smallest dosage which effectively and reliably prevents or minimizes the neurotoxic manifestations caused by that NMDA antagonist. Such neurotoxic manifestations, and the dosage of a candidate 5HT-2A agonist which can avoid such toxic manifestations, can be determined by tests on rodents or primates which search for cellular manifestations in the brain, such as vacuole formation, mitochondrial damage, heat shock protein expression, or other pathomorphological changes in neurons of the cingulate and retrosplenial cerebral cortices.

These cellular changes can also be correlated with abnormal behavior in lab animals. In human patients, since direct examination of brain tissue is not feasible, the appearance of hallucinations or other psychotomimetic symptoms, such as severe disorientation or incoherence, should be regarded as signals indicating that potentially neurotoxic damage is being generated in the CNS by an NMDA antagonist. Additionally, various types of imaging techniques (such as positron emission tomography and magnetic resonance spectroscopy, which use labelled substrates to identify areas of maximal activity in the brain) may also be useful for determining preferred dosages of 5HT-2A agonists for use as described herein, with or without NMDA antagonists.

The compositions of this invention may be administered by any suitable route which will introduce the intended drug(s) into the bloodstream. Depending on the specific NMDA antagonist and/or 5HT-2A agonist being used, the main candidate routes of administration will generally include oral ingestion of tablets, capsules, or liquids; intramuscular or intravenous injection; subcutaneous implantation of slow-release devices or formulations or osmotic mini-pumps; transmembrane routes, such as lozenges, sublingual tablets or wafers, chewing gum, intranasal sprays, skin patches, or permeating lotions or ointments; and rectal suppositories, such as for non-physician administration to patients who cannot be relied upon to take their medicine. Such preparations are all well known in the pharmaceutical arts, and will comprise, as active ingredients, either (1) a 5HT-2A agonist alone, or (2) a 5HT-2A agonist in combination with an NMDA antagonist, and a pharmaceutically acceptable carrier. In general, injectable formulations are preferred for acute crisis situations, while oral formulations are preferred for long-term administration.

In making such compositions, the active ingredient or ingredients will usually be mixed with and diluted by a carrier, or enclosed within a carrier such as a capsule. When the carrier serves as a diluent, it may be a solid, semisolid or liquid material which acts as a vehicle, excipient or medium for the active ingredient. Thus the composition can be in the form of tablets, pills, capsules, powders, lozenges, chewing gum, cachets, elixirs, emulsions, solutions, syrups, suspensions, Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propyl-hydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

For oral administration, the compositions of this invention can be admixed with carriers and diluents molded or pressed into tablets or enclosed in gelatin capsules. Alternatively, the mixtures can be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated or packaged in a unit dosage form, each dosage unit containing an effective amount of one or more 5HT-2A receptor agonists. The term "unit dosage form" refers to physically discrete units (such as capsules, tablets, or loaded syringe cylinders) suitable as unitary dosages for human subjects and other mammals, each unit containing a predetermined quantity of active material or materials calculated to produce the desired therapeutic effect, in association with the required pharmaceutical carrier. The amount of 5HT-2A receptor agonist preferred for a unit dosage will depend upon the amount and potency of the NMDA antagonist being administered (if any), or upon the severity of the psychotic onset symptoms being observed in a schizophrenic or other patient, and upon the efficacy of the given 5HT-2A agonist.

Except when responding to acute events such as stroke, cardiac arrest, or drowning, when higher dosages may be required, the preferred dosage of a 5HT-2A agonist will usually lie within the range of from about 0.001 to about 1000 mg, more usually from about 0.01 to about 500 mg per day. The amount of the NMDA antagonist will also depend upon the efficacy of the NMDA antagonist but will typically be within the range of from about 0.001 to about 1000 mg, more usually from about 0.01 to about 500 mg per day. It should be understood that the amount of any such compound actually administered will be determined by a physician, in the light of the relevant circumstances that apply to an individual patient (including the condition or conditions to be treated, the choice of composition to be administered, including the particular 5HT-2A agonist or the particular NMDA antagonist, the age, weight, and response of the individual patient, the severity of the patient's symptoms, and the chosen route of administration). Therefore, the above dosage ranges are intended to provide general guidance and support for the teachings herein, but are not intended to limit the scope of the invention.

Researchers are also developing ways to diagnose schizophrenia before it begins to manifest outward symptoms, using means such as family histories of schizophrenia, brain scans using positron emission tomography, magnetic resonance imaging, and magnetic resonance spectroscopy, and chromosomal analysis in an effort to identify genes that serve either as markers or causative factors. Some of these efforts have already met with some success, and the success rates will increase as more research is done. Accordingly, the 5HT-2A agonists described herein can be used to treat people who have been diagnosed as suffering from latent schizophrenia, or from an elevated risk of schizophrenia.

Salts, Isomers, and Analogs

The terms salt, isomer, and analog are used herein in their conventional pharmacological sense.

The term "salts" can include alkali metal salts as well as addition salts of free acids or free bases. Examples of acids which may be employed to form pharmaceutically acceptable acid addition salts include inorganic acids such as hydrochloric acid, sulfuric acid and phosphoric acid, and organic acids such as maleic acid, succinic acid and citric acid. Alkali metal salts or alkaline earth metal salts might include, for example, sodium, potassium, calcium or magnesium salts. All of these salts may be prepared by conventional means. The nature of the salt is not critical, provided that it is non-toxic and does not substantially interfere with the desired activity.

The term "isomer" as used herein includes regular chemical isomers as well as purified stereoisomers, in which certain pendant groups are coupled to a chiral carbon atom in a certain spatial configuration, to give the resulting molecule either a dextrorotatory or levorotatory configuration. It is common that a certain stereoisomer of a known drug will have a higher level of activity at a certain receptor than the other stereoisomer.

The term "analog" is used herein to refer to a molecule that structurally resembles a referent molecule (such as lisuride) but which has been modified in a targeted and controlled manner, by replacing a specific substituent of the referent molecule with an alternate substituent, such as a methyl or ethyl group, a hydroxyl group, etc. Such substituents are limited to groups having relatively low molecular weights, such as alkyl or aryl groups, nitrogen-containing moieties such as amine groups, etc. The term "analogs" does not include bifunctional conjugates, in which a first molecular structure having a first pharmaceutical activity is coupled to a second molecular structure having a second and different pharmaceutical activity, to provide a combined molecule having both activities. Instead, analogs are limited to molecular structures that have been slightly modified (often called "tweaked") to provide an improvement in a known and desired pharmacological activity. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

EXAMPLES

Example 1

Protection Against MK-801 Side Effects By 5HT-2A/2C Agonists

This example illustrates the neurotoxic side effects of the NMDA antagonist MK-801 (dizocilpine maleate), and the ability of various 5HT-2A/2C receptor agonists to prevent those toxic side effects. LSD, DOB, and DOM were obtained from the Research Technology Branch of the National Institute for Drug Abuse (NIDA, one of the institutes of the National Institutes of Health). DOI was purchased from Research Biochemicals International (Natick, Mass.).

Adult female rats received MK-801 (0.5 mg/kg) injected subcutaneously (sc), together with one of several test agents (LSD, DOB, DOI, DOM) injected into the intraperitoneal (ip) region at various doses. Control animals received MK-801 (0.5 mg/kg sc) and either dimethyl sulfoxide (DMSO) or saline, the vehicles used to dissolve the test agents. For each test agent, at least 20 rats were used, and at least four dosages were tested. The dose of MK-801 used in these tests has been shown previously to consistently and reliably induce, in treated rats, a fully developed neurotoxic reaction consisting of acute vacuole formation in the majority of pyramidal neurons in layers III and IV of the posterior cingulate (PC) and retrosplenial (RS) cortices.

The rats were sacrificed four hours after drug administration, and brain tissue from the PC/RS region was histopathologically evaluated by previously described methods using double-blinded techniques (Olney et al 1991). The number of vacuolated PC and RS neurons were counted on each side of the brain at a rostrocaudal level immediately posterior to where the corpus callosum ceases decussating across the midline (approximately 5.6 mm caudal to Bregma; Paxinos & Watson, *The Rat Brain in Stereotaxic Coordinates*, 2d Ed., 1986).

In previous tests (described in Farber et al 1995) the Applicants had found that the toxic reaction approaches maximal severity at this level and does not vary much in severity from one animal to another. Percentage reduction in neurotoxicity was calculated by dividing the mean number of vacuolated neurons in a specific experimental group, by the mean number in the control animals which received MK-801 but no 5HT-2A/2C agonist; the result was subtracted from one and multiplied by 100 to generate a percentage figure. Linear regression analysis was used to determine an $ED_{50}$ (i.e., the dose of a given 5HT-2A/2C agonist that reduced the mean number of vacuolated neurons to 50% of the control mean); the 25th and 75th percentiles were also recorded, to indicate confidence limits.

All control animals developed a neurotoxic reaction to MK-801 (mean number of vacuolated neurons per section= 223±10.5 SEM; n=26).

All 5HT-2A/2C agonists prevented (in a dose-dependent manner) the neurotoxic action of MK-801. Of the various 5HT-2A/2C agents tested, DOB was the most potent with an $ED_{50}=0.36$ mg/kg. LSD, DOM, and DOI were also effective but were slightly less potent, with $ED_{50}$'s of 0.68 mg/kg, 0.81 mg/kg and 1.05 mg/kg, respectively. These results are summarized in Table 1.

TABLE 1

Efficacy of 5HT-2A/2C Agonists in Blocking MK-801 Neurotoxicity

| Test Compound | $ED_{50}$ (mg/kg, ip) | Confidence Limits (25th & 75th percentiles) |
| --- | --- | --- |
| DOB | 0.36 | (0.17–0.79) |
| LSD | 0.67 | (0.13–3.46) |
| DOM | 0.81 | (0.27–2.39) |
| DOI | 1.05 | (0.41–2.68) |

Example 2

Use Of 5HT-2A/2C Antagonists To Confirm 5HT-2A/2C Receptor Role

The following example confirms that the neuroprotective effects provided by 5HT-2A/2C agonists are mediated through either the 5HT-2A or 5HT-2C receptor (or both), rather than through cross-reactivity at some other receptor or through some other mechanism. This was done by showing that these neuroprotective effects are blocked by selective 5HT-2A/2C antagonists.

Adult female rats received MK-801 (0.5 mg/kg sc) plus a combination of various doses of the 5HT-2A/2C agonist DOI, and a fixed dose of ritanserin (0.03 mg/kg ip). Ritanserin is an antagonist drug that selectively blocks activation of 5HT-2A/2C receptors. Accordingly, ritanserin can prevent DOI or other agents which act through 5HT-2 receptors from exerting a safening effect that can prevent vacuole formation when MK-801 is administered.

The brains were processed and the severity of damage was assessed as described in Example 1. Results were analyzed by analysis of covariance (ANCOVA) where the dose of DOI was the covariate and the presence of ritanserin served as the classification (treatment) variable. The homogeneity of slopes assumption was tested by determining whether there was a significant interaction between the covariate and the treatment variable.

Figure 3:
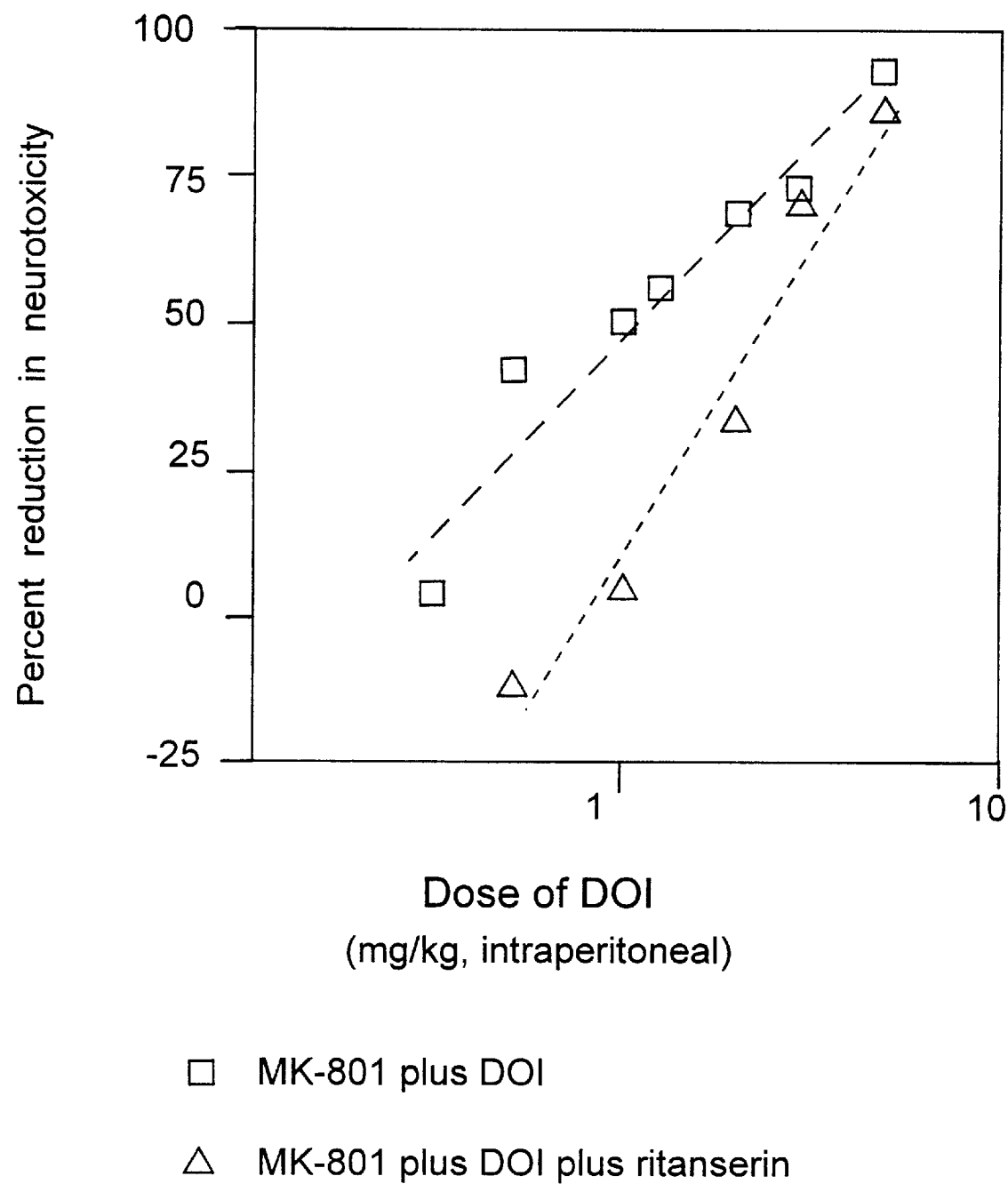
FIG. 3 illustrates that ritanserin (a 5HT-2A/2C antagonist) competitively blocks DOI's protective effects against the toxic side effects of MK-801, a potent NMDA antagonist drug. This confirms that agonist activity at 5HT class 2 receptors can help reduce or prevent NR/hypo-mediated neurotoxicity.

When a fixed dose of ritanserin (0.03 mg/kg ip) was administered together with various doses of DOI to MK-801-treated rats, ritanserin significantly interfered with DOI's protection $[F(1,84)=23.36, p<0.0005]$ and shifted the blocking curve to the right, as shown in FIG. 3. Data points in FIG. 3 represent the percent reduction in neurotoxicity, calculated as described in Example 1. This effect is consistent with a competitive interaction between DOI and ritanserin at 5HT-2A/2C receptor sites.

Similar shifts of the curves to the right was seen in similar tests using a small number of animals treated with ritanserin plus another 5HT-2A/2C agonist, LSD (n=4), and in still other animals treated with ketanserin (a 5HT-2A/2C antagonist similar to ritanserin) plus DOI (n=5).

Example 3

Confirmation That 5HT-2A Agonist Action, Rather Than 5HT-2C Agonist Action, Is The Protective Mechanism To clarify whether the protection conferred by LSD, DOI, DOB and DOM can be attributed to agonist action at the 5HT-2A or the 5HT-2C receptor (or both), the Applicants tested lisuride (purchased from Research Biochemicals International, Natick, Mass.). This drug is widely used in Europe, and is a 5HT-2A agonist but a 5HT-2C antagonist. Lisuride potently protected against the neurotoxic action of MK-801 ($ED_{50}=0.17$ mg/kg; n=45) indicating that an agonist action at the 5HT-2A receptor is the most likely mechanism to explain the protective action of this class of compounds.

To further corroborate that the 5HT-2A receptor is the apparent site at which certain serotonin agonists block NMDA antagonist neurotoxicity, the Applicants also tested an experimental compound called SDZ SER-082, a selective 5HT-2C antagonist (provided to the Applicants by Sandoz Laboratories). It is described in Nozulak et al 1993. It did not affect MK-801 neurotoxicity, either positively or negatively (n=22).

In other tests, DOI (n=29) was found to protect against NMDA antagonist toxicity even when SDZ SER-082 was added to block the effects of DOI at the 5HT-2C receptor.

These two findings, taken together, indicate that neither agonist nor antagonist activity at the 5HT-2C receptor site is involved in the ability of 5HT-2A agonists to prevent MK-801 neurotoxicity.

Example 4

Non-Interference With NMDA Antagonist Activity At NMDA Receptors

Several tests were performed to ensure that when a 5HT-2A agonist is administered together with an NMDA antagonist, the 5HT-2A agonist will not interfere with the activity of the NMDA antagonist drug at NMDA receptors.

These experiments were performed using segments of chick embryo retina. This is a widely used model for studying the production and prevention of excitotoxic phenomena, since it is simple and inexpensive. Chick tissue is used, since it tends to provide a better model of adult mammalian tissue than embryonic or juvenile mammalian tissue. Unlike newborn mammals, which are usually blind at birth, baby chicks can see quite well as soon as they emerge from the shell, and the NMDA receptors in chick retinal tissue are fully mature and functional.

In these tests, NMDA was introduced into the incubation medium in a concentration (40 $\mu$M) sufficient to produce a fully developed excitotoxic lesion within 30 min, displaying acute degeneration and necrosis of the majority of neurons in the inner layers of the retina. The control retinas were incubated with NMDA alone, and experimental retinas were incubated with NMDA plus MK-801 in sufficient concentration (500 nM) to completely block the NMDA receptors and prevent excitotoxic lesions from developing. Additional experimental retinas were incubated with NMDA plus MK-801 plus either of two 5HT-2A agonists (LSD or DOI), in a wide range of concentrations (500 nM to 100 $\mu$M).

The results were that all retinas incubated in NMDA alone (n=6) had well developed acute lesions affecting the inner neural layers of the retina and extending across the full width of the retina. In contrast, retinas incubated in NMDA plus MK-801, either with or without various concentrations of the 5HT-2A agonists, showed no cytopathology (n=6 retinas per treatment condition). Thus, the NMDA antagonist MK-801 completely protected against excitotoxic damage, regardless of whether a 5HT-2A agonist was present in the incubation medium. The 5HT-2A agonists did not block the useful protective effects of the NMDA antagonist.

Example 5

Screening Of Anti-Psychotic Drugs And Sigma Blockers For Protection Against MK-801 Side effects After recognizing that several correlations exist between a neurotoxic NR/hypo condition caused by NMDA antagonist drugs, and similar NR/hypo conditions that apparently occur as a disease process in schizophrenic patients, the Applicants decided to screen several drugs that have either proven or putative antipsychotic effects and are considered potentially useful as anti-schizophrenia drugs, to determine whether such drugs would block the neurotoxic side effects of NMDA antagonists such as MK-801.

Several of the antipsychotic agents tested (haloperidol, thioridazine and loxapine) are known to interact with both dopamine receptors and sigma receptors. At least one drug with putative antipsychotic effects (rimcazole) is more selective, and has substantial affinity only for sigma receptors. Three others (clozapine, fluperlapine, and olanzapine) often referred to as "atypical" antipsychotic agents were also tested, and shown to reduce vacuole formation. In addition, di(2-tolyl)guanidine was also tested and shown to block vacuole formation; it is not regarded as an anti-psychotic agent, but it is known to block sigma receptors.

In these tests, neurotoxic side effects (measurable as vacuoles and other neuronal damage in PC/RS cortical neurons in rats) were elicited by administering MK-801 to rats, as described in Example 1. Control animals received saline or DMSO, but no anti-psychotic drugs. Test animals were injected ip with an antipsychotic drug, listed above and in Table 2. Vacuoles were counted and data were processed as described in Example 1.

The results, shown in Table 2, indicate that all but one of the compounds tested were active, at varying $ED_{50}$ doses, in protecting against the toxic side effects of NMDA receptor hypofunction (NR/hypo). The single exception was sulpiride, which was inactive; this may have been because the sulpiride was administered only 15 minutes prior to addition of MK-801, and it was subsequently learned by the Applicants that sulpiride apparently takes several hours to penetrate into the CNS.

Since the various agents which were effective in blocking NMDA antagonist neurotoxicity in this study are agents that have either proven or putative antipsychotic activity, these results are consistent with the conclusion that compounds which can block NR/hypo neurotoxicity induced by NMDA antagonist drugs in laboratory animals are also likely to be effective in treating similar types of NR/hypo-related neurotoxicity which occur as a component of idiopathic psychotic illnesses such as schizophrenia.

TABLE 2

EFFECTS OF VARIOUS ANTI-PSYCHOTIC DRUGS IN PROTECTING AGAINST NR/hypo-INDUCED VACUOLES

| TEST COMPOUND | $ED_{50}$ (MG/KG, ip) | CONFIDENCE LIMITS (25th & 75th percentiles) |
|---|---|---|
| Olanzapine | 1.4 | (0.7–2.6) |
| Fluperlapine | 2.3 | (1.5–3.5) |
| Clozapine | 3.2 | (1.1–9.7) |
| Haloperidol | 5.1 | (2.4–10.9) |
| Rimcazole | 17.8 | (8.9–35.6) |
| Di(2-tolyl) guanidine | 22.2 | (15.0–33.3) |
| Loxapine | 23.6 | (3.9–140.6) |
| Thioridazine | 55.3 | (25.0–122.2) |
| Amoxapine | 75.0 | (55.7–100.9) |
| Sulpiride | >200.0 | Inactive |

Example 6

Additional Tests To Confirm The Link Between NR/hypo AND Schizophrenia

Several additional tests were carried out to explore the correlation between NMDA receptor hypofunction (NR/hypo) and schizophrenia. In one set of tests, minipumps were implanted subcutaneously in a number of rats, to continuously administer MK-801 at a low dosage (83 μg/kg/hour) for 5 days. The dose delivered on any single day was not enough to kill neurons if delivered in a single bolus; however, continuous slow delivery of the drug at these dosages over a prolonged period of time resulted in a relatively widespread pattern of evolving disseminated brain damage primarily affecting certain limbic brain regions that also have been reported to show pathological changes in the brains of schizophrenic humans autopsied after death.

This result provides yet another link which connects schizophrenia to chronic NR/hypo as a causative mechanism.

In addition, this subchronic delivery approach provides a model that mimics the way in which NMDA receptor hypofunction can gradually and insidiously damage the brain in schizophrenia. This laboratory model can be used to compare the efficacy of candidate 5HT-2A agonist drugs (or other classes of drugs) in preventing the damage caused by schizophrenia.

Example 7

Tests Showing Involvement Of Sigma, Muscarinic, And Non-NMDA Receptors In NR/hypo Toxicity A set of tests was carried out by the Applicants, to help elucidate the role of various neuronal systems in the toxic side effects caused by NR/hypo. In these tests, combinations of several receptor agonists were microinjected into the cingulate cortex (this type of direct injection into the brain avoided problems of limited permeability of certain drugs through blood-brain barriers). These test drugs included (1) (+)SKF-10,047, an agonist that stimulates activity at sigma receptors; (2) carbachol, an agonist that stimulates activity at muscarinic-type acetylcholine receptors; and (3) kainic acid, an agonist which stimulates non-NMDA glutamate receptors. In some test animals, only one of these drugs was injected. In other animals, various combinations of two drugs were injected (mixed together in a "cocktail"). In still other animals, all three drugs were injected, mixed together.

In animals injected with all three drugs, a neurotoxic reaction was found in cingulate cortical neurons, which was identical to the toxic reaction that is caused by subcutaneous administration of MK-801, an NMDA antagonist. However, in animals injected with only two (or only one) of the three drugs, no such toxic reaction was found.

These results indicate that NMDA antagonist neurotoxicity involves excessive activation of all three of these receptor systems (i.e., sigma receptors, muscarinic-type cholinergic receptors, and non-NMDA glutamate receptors). These results helped establish the neuronal circuitry that is described in the Background section and shown in schematic form in FIG. 1.

From the finding that it requires excessive activation of all three systems for NR/hypo-mediated pathomorphological brain changes to occur, it follows that blockade of any one of these systems would prevent such permanent brain damage. However, the Applicants believe that, in at least some cases, excessive activation of any one or two of these systems may be sufficient to trigger transient mental aberrations, such as hallucinations, from which it follows that for optimal clinical management of psychotic symptoms and mental aberrations in schizophrenia, it may be necessary to block at least two or possibly all three of these receptor systems in some cases.

Thus, there has been shown and described a new and useful means for allowing the safe use of NMDA antagonists for purposes such as preventing excitotoxic brain damage, treating neuropathic pain, and preventing development of tolerance to addictive drugs. There has also been disclosed a new and useful method for treating and preventing schizophrenic brain damage. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

For countries that do not allow patent coverage of medical treatments, on the asserted ground that such treatments are humanitarian rather than industrial, it should be noted that this invention has industrial utility, in allowing the industrial manufacture (preparation) and sale of medicaments for treating pathological processes associated with NMDA receptor hypofunction, and for treating certain other conditions such as neuropathic or chronic pain.

REFERENCES

Backonja, M., et al, "Response of chronic neuropathic pain syndromes to ketamine: a preliminary study," *Pain* 56: 51–57 (1994)

Ben-Eliyahu, S., et al, "The NMDA receptor antagonist MK-801 prevents long-lasting non-associative morphine tolerance in the rat," *Brain Research* 575: 304–308 (1992)

Bersani, G., et al, "Neuroleptic-induced extrapyramidal side effects: clinical perspectives with ritanserin (R55 667), a new selective 5-HT2 receptor blocking agent," *Clin Ther Res* 40: 492–499 (1986)

Bjerkenstedt, L., "Melperone in the treatment of schizophrenia," *Acta Psychiatr Scand* 352 [suppl]: 35–39 (1989)

Bloom F. E., Kupfer D J (eds): *Psychopharmacology—The Fourth Generation of Progress*, Raven Press, New York, 1995.

Boast, C. A., "Neuroprotection after brain ischemia: role of competitive NMDA antagonists," *Neurology and Neurobiology* 46: 691–698 (1988)

Burris, K. D. et al, "(+)Lysergic Acid Diethylamide, but not Its Nonhallucinogenic Congeners, Is a Potent Serotonin 5HT1C Receptor Agonist," *J Pharmacol Exp Ther* 258: 891–896 (1991)

Carter, C., et al, "Ifenprodil and SL 82.0715 as cerebral anti-ischemic agents. II. Evidence for N-methyl-D-aspartate receptor antagonist properties," *J Pharmacol Exptl Ther* 247: 1222–1232 (1988)

Ceulemans, D. L. S., et al., "Effect of serotonin antagonism in schizophrenia: A pilot study with setoperone," *Psychopharmacology* 85: 329–332 (1985)

Choi, D. W., "Glutamate neurotoxicity and diseases of the nervous system," *Neuron* 1: 623–634 (1988)

Choi, D. W., "Excitotoxic cell death," *J Neurobiol* 23: 1261–1276 (1992)

Corso, T. D., et al, "Neuron necrotizing properties of phencyclidine," *Soc Neurosci Abst* 20: 1531 (1994)

Davar, G., et al, "MK-801 blocks the development of thermal hyperalgesia in a rat model of experimental painful neuropathy," *Brain Res* 553: 327–330 (1991)

Fagg, G. E., et al, "CGP 37849 and CGP 39551: novel competitive NMDA receptor antagonists with potent oral anticonvulsant activity," *Prog Clin Biol Res* 361: 421–7 (1990)

Ferkany, J. W., et al, "Pharmacological profile of NPC 12626, a novel, competitive NMDA receptor antagonist," *J Pharmacol Exp Ther* 250: 100–109 (1989)

Ferkany, J. W., et al, "Pharmacological profile of NPC 17742 [2R, 4R, 5S-(2-amino-4,5-(1,2-cyclohexyl)-7-phosphonoheptanoic acid)], a potent, selective and competitive N-methyl-D-aspartate receptor antagonist," *J Pharmacol Exp Ther* 264: 256–64 (1993)

Fiorella, D. et al, "The Interactions of Typical and Atypical Antipsychotics with the (−)2,5,-Dimethoxy-4-Methamphetamine (DOM) Discriminative Stimulus," *Neuropharmacology* 34: 1297–1303 (1995a)

Fiorella, D. et al, "The Role of the 5-HT2A and 5-HT2C Receptors in the Stimulus Effects of Hallucinogenic Drugs I: Antagonist Correlation Analysis," *Psychopharmacology* 121: 347–356 (1995b)

Fiorella, D. et al, "Role of 5-HT2A and 5-HT2C Receptors in the Stimulus Effects of Hallucinogenic Drugs II: Reassessment of LSD False Positives," *Psychopharmacology* 121: 357–363 (1995c)

Gelders, Y. G., et al, "Serotonin-S2 blockers in the treatment of chronic schizophrenia," *Clin Neuropharmac* 9: 325–327 (1986)

Grotta, J., et al., "Safety and tolerability of the glutamate antagonist CGS 19755 (Selfotel) in patients with acute ischemic stroke: Results of a phase IIa randomized trial," *Stroke* 26: 602–605 (1995)

Gustafson, B. and Christensson, E., "Amperozide—a new putatively antipsychotic drug with a limbic mode of action on dopamine mediated behavior," *Pharmacol Toxicol* 1 [suppl]: 12–17 (1990)

Hargreaves, R. J., et al, "Competitive as well as uncompetitive NMDA receptor antagonists affect cortical neuronal morphology and cerebral glucose metabolism," *Neurochem Research* 18: 1263–1269 (1993)

Herrling, P. L. "D-CPPene (SDZ EAA 494), a competitive NMDA antagonist: Results from animal models and first results in humans," *Neuropsychopharmacology* 10, No 3S/Part 1: 591S (1994) Javitt, D. C. and Zukin, S. R., "Recent Advances in the Phencyclidine Model of Schizophrenia," *Am J Psychiat* 148: 1301–1308 (1991)

Kehne, J. H., et al, "Preclinical characterization of the potential of the putative atypical antipsychotic MDL 100, 907 as a potent 5HT-2A antagonist with a favorable CNS safety profile," *J Pharmacol Exp Ther* 277: 968–981 (1996)

Kristensen, et al, "The NMDA-receptor antagonist CPP abolishes neurogenic 'wind-up pain' after intrathecal administration in humans," *Pain* 51: 249–253 (1992)

Krystal, J. H., et al, "Subanesthetic effects of the non-competitive NMDA antagonist, ketamine, in humans: Psychotomimetic, perceptual, cognitive and neuroendocrine responses," *Arch Gen Psychiatry* 51: 199–214 (1994)

Kuoppamaki, M. Et al, "differential regulation of rat 5HT-2A and 5HT-2C receptors after chronic treatment with clozapine, chlorpromazine and three putative atypical antipsychotic drugs," *Neuropsychopharmacology* 13: 139–150 (1995)

Leysen, J. E., et al., "Receptor binding properties in vitro and in vivo of ritanserin: A potent and long acting serotonin-2 antagonist," *Mol Pharmacol* 27: 600–611 (1985)

Mao, J, et al, "Intrathecal MK-801 and local nerve anesthesia synergistically reduce nociceptive behaviors in rats with experimental peripheral mononeuropathy," *Brain Res.* 576: 254–262 (1992)

Marek, P., et al, "Excitatory amino acid antagonists (kynurenic acid and MK-801) attenuate the development of morphine tolerance in the rat," *Brain Research* 547: 77–81 (1991)

Martin, G. R. and Humphrey, P. P. A., "Receptors for 5-hydroxytryptamine: current perspectives on classification and nomenclature," *Neuropsychopharmacology* 33: 261–273 (1994)

Massieu, L., et al, "A comparative analysis of the neuroprotective properties of competitive and uncompetitive N-methyl-D-aspartate receptor antagonists in vivo: implications for the process of excitotoxic degeneration and its therapy," *Neuroscience* 55: 883–92 (1993)

Mendels, J., "The effect of methysergide (a serotonine agent) on schizophrenia: a preliminary report," *Br J Psychiatry* 124: 157–160 (1967)

Neugebauer, V., et al, "The clinically available NMDA receptor antagonist memantine is antinociceptive on rat spinal neurones," *NeuroReport* 4: 1259–1262 (1993)

Nozulak J, et al, "SDZ SER 082, a centrally acting and selective 5-ht-2c antagonist," *Soc Neurosci Abstr* 1993, 19:298.

Ohuoha, D. C., et al, "The role of serotonin in schizophrenia: an overview of the nomenclature, distribution and alterations of serotonin receptors in the central nervous system," *Psychopharmacology* 112: S5–S15 (1993)

Olney, J. W., "Glutamate," pp. 468–470 in *Encyclopedia of Neuroscience*, G. Adelman, ed. (Birkhauser, Boston, 1987)

Olney, J. W., et al, "Pathological changes induced in cerebrocortical neurons by phencyclidine and related drugs," *Science* 244: 1360–1362 (1989)

Olney, J. W., "Excitotoxic amino acids and neuropsychiatric disorders," pp 47–71 in *Annual Review of Pharmacology and Toxicology*, Volume 30, R. George, et al, eds. (Annual Reviews, Inc, Palo Alto, Calif., 1990)

Olney, J. W., et al, "NMDA antagonist neurotoxicity: Mechanism and prevention," *Science* 254: 1515–1518 (1991)

Schmidt, C. J. et al, "Minireview: The role of 5HT-2A receptors in antipsychotic activity," *Life Sciences* 56: 2209–2222 (1995)

Seltzer, Z., et al, "Modulation of neuropathic pain behavior in rats by spinal disinhibition and NMDA receptor blockade of injury discharge," *Pain* 45: 69–75 (1991)

Sershen, H., et al, "Ibogaine reduces preference for cocaine consumption in C57BL/6By mice," *Pharmacol Biochem Behav* 47: 13–19 (1994)

Siegel, G. J., et al, eds., *Basic Neurochemistry* (Fifth Edition, Raven Press, New York, 1994)

Tal, M. and Bennett, G. J., "Dextrorphan relieves neuropathic heat-evoked hyperalgesia in the rat," *Neuroscience Letters* 151: 107–110 (1993)

Titeler, M., et al, "Radioligand binding evidence implicates the brain 5HT-2 receptor as a site of action for LSD and phenylisopropylamine hallucinogens," *Psychopharmacology* 94: 213–216 (1988)

Trujillo, K. A. and Akil, H., "Inhibition of morphine tolerance and dependence by the NMDA receptor antagonist MK-801, " *Science* 251: 85–87 (1991)

Woolf, C. J., "Recent advances in the pathophysiology of acute pain," *Br J Anaesth.* 63: 139–146 (1989)

Yamamoto, T. and Yaksh, T. L., "Spinal pharmacology of thermal hyperesthesia induced by constriction injury of sciatic nerve: Excitatory amino acid antagonists," *Pain* 49: 121–128 (1992)

Zeigler, D., et al, "transdermal clonidine versus placebo in painful diabetic neuropathy," *Pain* 48: 403–408 (1992)

Zifa, E. and Fillion, G., "5-hydroxytryptamine receptors," *Pharmacological Reviews* 44: 401–458 (1992)

We claim:

1. A method for treating a patient, comprising the step of administering, to a mammalian patient in need thereof, a combination of:
    (a) a pharmacologically acceptable NMDA antagonist drug which penetrates mammalian blood-brain barriers, in a quantity that is therapeutically effective in providing a benefit selected from the group consisting of (i) reducing excitotoxic damage to neurons, (ii) treating neuropathic pain, and (iii) preventing tolerance or addiction to opiate analgesics; and,
    (b) a pharmacologically acceptable 5HT-2A agonist drug which stimulates activity at 5HT-2A serotonin receptors, and which does not cause hallucinations, and which penetrates mammalian blood-brain barriers, in an amount that is therapeutically effective for inhibiting adverse neurological effects that would be caused by the NMDA antagonist drug in the absence of the 5HT-2A agonist drug.

2. The method according to claim 1 wherein the 5HT-2A agonist drug is selected from the group consisting of lisuride, salts of lisuride, and pharmaceutically acceptable isomers and analogs of lisuride which stimulate activity at 5HT-2A serotonin receptors but which do not stimulate activity at 5HT-2C serotonin receptors at a level sufficient to cause hallucinations.

3. The method according to claim 1 wherein the 5HT-2A agonist drug is administered in a dosage that has been shown to be therapeutically effective for inhibiting at least one adverse neurological effect selected from the group consisting of:
    (a) formation of vacuoles in neurons in cerebrocortical or limbic brain regions;
    (b) expression of heat shock proteins in cerebrocortical or limbic brain regions;
    (c) alteration or loss of mitochondria in neurons;
    (d) neuronal death;

(e) hallucinations; and, (f) abnormal behavioral displays in laboratory animals.

4. The method according to claim 1 wherein the NMDA antagonist drug and the 5HT-2A agonist drug are administered to the patient in order to reduce excitotoxic neuronal damage caused by an acute insult to the patient's central nervous system, without causing neurotoxic side effects.

5. The method according to claim 1 wherein the NMDA antagonist drug and the 5HT-2A agonist drug are administered to the patient in order to reduce neuronal damage associated with a progressive neurodegenerative disease, without causing neurotoxic side effects.

6. The method according to claim 1 wherein the NMDA antagonist drug and the 5HT-2A agonist drug are administered to the patient in order to reduce neuropathic pain, without causing neurotoxic side effects.

7. The method according to claim 1 wherein the NMDA antagonist drug and the 5HT-2A agonist drug are administered to the patient in order to suppress development of tolerance to a potentially addictive drug, without causing neurotoxic side effects.

8. In the method of administering an NMDA antagonist drug to a patient in need thereof for a therapeutic purpose, the improvement wherein a pharmacologically acceptable 5HT-2A agonist drug which penetrates mammalian blood-brain barriers and which does not cause hallucinations is also administered to the patient, in an amount effective in inhibiting adverse neurological effects that would be caused by the NMDA antagonist drug in the absence of the 5HT-2A agonist drug.

9. The method according to claim 8 wherein the 5HT-2A agonist drug is selected from the group consisting of lisuride, salts of lisuride, and pharmaceutically acceptable isomers and analogs of lisuride which stimulate activity at 5HT-2A serotonin receptors but which do not stimulate activity at 5HT-2C serotonin receptors at a level sufficient to cause hallucinations.

10. The method according to claim 8 wherein the 5HT-2A agonist drug is administered in a dosage that has been shown to be therapeutically effective for inhibiting at least one adverse neurological effect selected from the group consisting of:

(a) formation of vacuoles in neurons in cerebrocortical or limbic brain regions;

(b) expression of heat shock proteins in cerebrocortical or limbic brain regions;

(c) alteration or loss of mitochondria in neurons;

(d) neuronal death;

(e) hallucinations in humans; and, (f) abnormal behavioral displays in laboratory animals.

11. The method according to claim 8 wherein the NMDA antagonist drug and the 5HT-2A agonist drug are administered to the patient in order to reduce excitotoxic neuronal damage caused by an acute insult to the patient's central nervous system, without causing neurotoxic side effects.

12. The method according to claim 8 wherein the NMDA antagonist drug and the 5HT-2A agonist drug are administered to the patient in order to reduce neuronal damage associated with a progressive neurodegenerative disease, without causing neurotoxic side effects.

13. The method according to claim 8 wherein the NMDA antagonist drug and the 5HT-2A agonist drug are administered to the patient in order to reduce neuropathic pain, without causing neurotoxic side effects.

14. The method according to claim 8 wherein the NMDA antagonist drug and the 5HT-2A agonist drug are administered to the patient in order to suppress development of tolerance to a potentially addictive drug, without causing neurotoxic side effects.

* * * * *